United States Patent
Pfeiffer et al.

(10) Patent No.: US 9,380,897 B2
(45) Date of Patent: *Jul. 5, 2016

(54) FLUID CONSUMPTION MONITORING SYSTEM

(71) Applicant: IQHYDR8, LLC, San Diego, CA (US)

(72) Inventors: James William Pfeiffer, Los Gatos, CA (US); Gerald Sweeney, La Jolla, CA (US); Cory McCluskey, Encinitas, CA (US)

(73) Assignee: IQHYDR8, LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/008,303

(22) Filed: Jan. 27, 2016

(65) Prior Publication Data

US 2016/0135626 A1     May 19, 2016

Related U.S. Application Data

(63) Continuation of application No. 14/741,202, filed on Jun. 16, 2015, which is a continuation-in-part of (Continued)

(51) Int. Cl.
| | |
|---|---|
| *A47G 19/22* | (2006.01) |
| *B65D 51/16* | (2006.01) |
| *G01F 17/00* | (2006.01) |

(52) U.S. Cl.
CPC ........ *A47G 19/2227* (2013.01); *B65D 51/1644* (2013.01); *G01F 17/00* (2013.01); *A47G 2019/225* (2013.01); *A47G 2019/2244* (2013.01)

(58) Field of Classification Search
CPC .............. A47G 19/2227; A47G 2019/225; A47G 2019/2244; B65D 51/1644; G01F 17/00

USPC ............... 220/703, 711, 714, 202, 203.01, 220/203.23, 203.04, 212, 303, 710.5, 713; 215/387, 260, 311, 315, 307; 206/217; 702/154; 340/573.1, 686.1

See application file for complete search history.

(56) References Cited

U.S. PATENT DOCUMENTS

| | | |
|---|---|---|
| 3,964,631 A | 6/1976 | Albert |
| 4,099,642 A | 7/1978 | Nergard |

(Continued)

FOREIGN PATENT DOCUMENTS

| | | |
|---|---|---|
| EP | 1292218 A1 | 4/2006 |
| EP | 2472488 A1 | 7/2012 |

OTHER PUBLICATIONS

Hydrachoach, Hydration Monitors, www.hydracoach.com, 2004, 2 pages.

(Continued)

*Primary Examiner* — Robert J Hicks
*Assistant Examiner* — Kareen Thomas
(74) *Attorney, Agent, or Firm* — Arc IP Law, PC; Joseph J. Mayo

(57) ABSTRACT

An activity and volume sensing beverage container cap system for a beverage container including a cap that couples with the beverage container, a processor, a timer and at least one activity level sensor, such as an inclinometer, coupled with the processor. The activity level sensor detects container orientation. When the container is tilted, the timer measures an amount of time in an orientation. Based on the current and previous orientation and the amount of time the container is in different orientations, the processor determines an amount of time of activity of the user, and a level of activity of the user, such as number of steps or moves per time. The inclinometer is also used to determine the amount of volume dispensed from the container when tilted over a threshold indicative of drinking. Thus one inclinometer may be utilized as both to determine activity level and volume of fluid dispensed.

20 Claims, 24 Drawing Sheets

Related U.S. Application Data application No. 14/555,616, filed on Nov. 27, 2014, which is a continuation-in-part of application No. 14/329,246, filed on Jul. 11, 2014, now Pat. No. 8,907,796, which is a continuation-in-part of application No. 14/305,537, filed on Jun. 16, 2014, now Pat. No. 9,151,605, which is a continuation-in-part of application No. 13/780,145, filed on Feb. 28, 2013, now abandoned.

(60) Provisional application No. 61/637,489, filed on Apr. 24, 2012, provisional application No. 61/608,306, filed on Mar. 8, 2012.

(56) References Cited

U.S. PATENT DOCUMENTS

| | | | |
|---|---|---|---|
| 4,419,016 A * | 12/1983 | Zoltan | A61J 7/0481 206/534 |
| 4,736,871 A | 4/1988 | Luciani et al. | |
| 6,062,419 A | 5/2000 | Kruger et al. | |
| 6,082,358 A | 7/2000 | Scarrott et al. | |
| 6,212,959 B1 | 4/2001 | Perkins | |
| 6,990,860 B1 | 1/2006 | Gillanders | |
| 7,011,227 B2 | 3/2006 | Ward et al. | |
| 7,020,508 B2 | 3/2006 | Stivoric et al. | |
| D547,607 S | 7/2007 | Forsman | |
| D584,566 S | 1/2009 | Fuller | |
| D586,184 S | 2/2009 | Miller et al. | |
| D592,913 S | 5/2009 | Pinelli et al. | |
| 7,783,344 B2 | 8/2010 | Lackey et al. | |
| D652,256 S | 1/2012 | Eyal | |
| 8,094,014 B2 | 1/2012 | Ransch | |
| D656,787 S | 4/2012 | Phillips et al. | |
| D657,618 S | 4/2012 | Wahl | |
| 8,272,532 B2 | 9/2012 | Michaelian et al. | |
| D675,059 S | 1/2013 | Carreno | |
| 8,360,267 B1 | 1/2013 | Chiou et al. | |
| 8,378,830 B2 | 2/2013 | Moran | |
| 8,397,940 B2 | 3/2013 | Steininger | |
| D679,541 S | 4/2013 | Samartgis | |
| 8,574,165 B2 | 11/2013 | Marsh | |
| D696,073 S | 12/2013 | Miller et al. | |
| 8,602,238 B2 | 12/2013 | El-Saden et al. | |
| 8,611,992 B2 | 12/2013 | Goldstein et al. | |
| D700,012 S | 2/2014 | Hurley et al. | |
| 8,734,341 B2 | 5/2014 | Howell et al. | |
| D707,124 S | 6/2014 | Blain et al. | |
| D707,492 S | 6/2014 | George et al. | |
| 2005/0115977 A1 | 6/2005 | Dibdin et al. | |
| 2006/0231109 A1 | 10/2006 | Howell et al. | |
| 2007/0048224 A1 | 3/2007 | Howell et al. | |
| 2007/0146154 A1 | 6/2007 | Teller | |
| 2008/0089993 A1 | 4/2008 | Hwang et al. | |
| 2009/0080180 A1 | 3/2009 | Bertken | |
| 2009/0250480 A1 | 10/2009 | Pinelli | |
| 2010/0270257 A1 * | 10/2010 | Wachman | G06Q 10/10 215/228 |
| 2011/0036801 A1 | 2/2011 | Krans et al. | |
| 2011/0050431 A1 | 3/2011 | Hood et al. | |
| 2011/0309095 A1 | 12/2011 | Pinelli | |
| 2012/0037651 A1 | 2/2012 | Steuer | |
| 2012/0094261 A1 | 4/2012 | Hayn et al. | |
| 2012/0259180 A1 | 10/2012 | Rock | |
| 2012/0265480 A1 | 10/2012 | Oshima | |
| 2013/0275075 A1 | 10/2013 | Johnson | |
| 2013/0319915 A1 | 12/2013 | Gellibolian et al. | |
| 2014/0182952 A1 | 7/2014 | Yuen et al. | |
| 2014/0221788 A1 | 8/2014 | Teller et al. | |
| 2014/0221792 A1 | 8/2014 | Miller et al. | |
| 2014/0249388 A1 | 9/2014 | Howell et al. | |
| 2014/0311239 A1 | 10/2014 | Marjanovic et al. | |
| 2015/0122688 A1 | 5/2015 | Dias et al. | |

OTHER PUBLICATIONS

Hydracoach, Hydracoach Intelligent Water Bottle User Guide, 2007, 14 pages.
Kickstarter, "Track your water intake and Hydrate better with the Hug", 2014, 16 pages.
Vessyl Design, Faq page, 2014, 7 pages.
Contigo, Innovation Web Page, www.gocontigo.com, 2015, 3 pages.
CafePress Travel Mug, Web Page, http://www.cafepress.com/+mugs?cat=203071, 2015, 2 pages.
International Search Report Received in PCT/US2015/036072, dated Sep. 4, 2015, 7 pages.

* cited by examiner

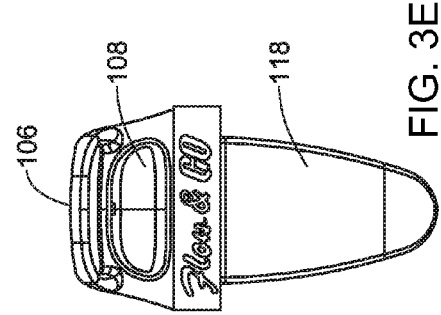
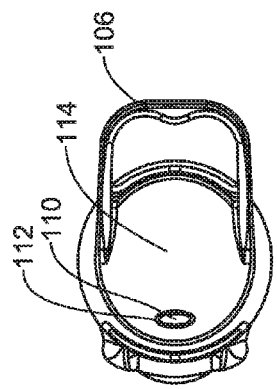
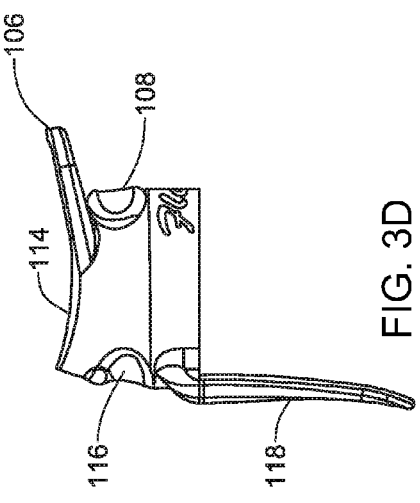
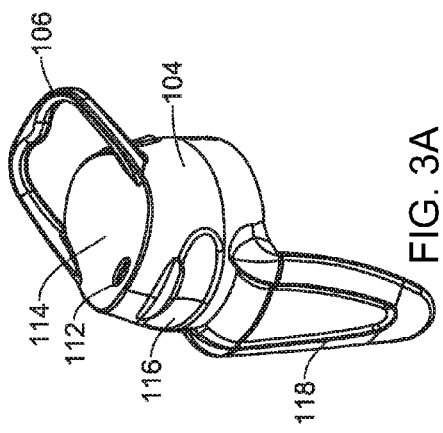
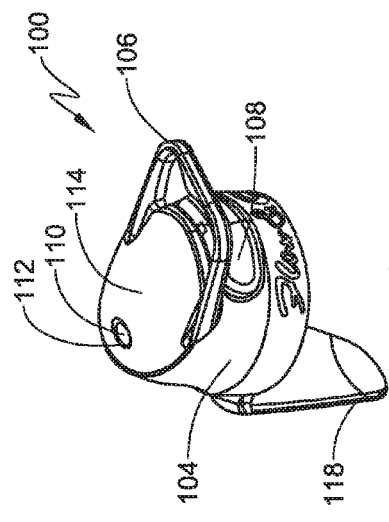

FLUID CONSUMPTION MONITORING SYSTEM

This application is a continuation of U.S. Utility patent application Ser. No. 14/741,202, filed Jun. 16, 2015, which is a continuation-in-part of U.S. Utility patent application Ser. No. 14/555,616, filed Nov. 27, 2014, which is a continuation-in-part of U.S. Utility patent application Ser. No. 14/329,246, filed Jul. 11, 2014, issued as U.S. Pat. No. 8,907,796, which is a continuation-in-part of U.S. Utility patent application Ser. No. 14/305,537, filed Jun. 16, 2014, which is a continuation in part of U.S. Utility patent application Ser. No. 13/780,145, filed Feb. 28, 2013, which claims the benefit of U.S. Provisional Patent Application No. 61/637,489 and U.S. Provisional Patent Application No. 61/608,306, the specifications of which are all hereby incorporated herein by reference.

BACKGROUND OF THE INVENTION

1. Field of the Invention

Embodiments of the invention generally relate to the field of beverage container valves, caps and containers. In particular, but not by way of limitation, one or more embodiments of the invention relates to a fluid consumption monitoring system for example that provides a reusable, washable beverage container cap for a beverage container that generally includes a cap, a flexible seal valve and an optional handle that may be used with a variety of different beverage containers autonomously and/or with a mobile device if available or both with autonomous operation and display and remote wireless operation and display of hydration associated information.

2. Description of the Related Art

Generally, beverage containers include reusable water bottles and other insulated and non-insulated beverage containers with removable caps of various types. Such beverage containers typically come in a wide variety of styles and configurations with caps ranging from simple threaded lids that must be completely removed to drink the beverage, to complex systems with straws, valves, and other mechanisms. Existing systems, however, have failed to meet the need for a beverage container and cap that is easy to carry, easy to use without unwanted spillage, and dishwasher safe. Typical beverage containers have further failed to meet the need to provide users with useful information during use of the container as part of various activities such as walking, hiking, biking, etc.

In addition, there are no known beverage containers that prompt a user to drink to maintain adequate hydration. For example there are no known beverage containers that economically measure an amount of time of activity, level of activity and the amount of liquid dispensed as most flow meters are expensive and also are difficult to clean or prevent the buildup of bacteria. There are also no known beverage containers that contain inclinometers, or position sensors, or orientation sensors, and timers to determine the amount of liquid dispensed in an indirect manner. There are no known systems that utilize a relatively inexpensive inclinometer in both cost and power to indicate activity level or the amount of volume an individual has consumed. There are no known beverage containers that contain an inclinometer, or other types of volume sensors including a capacitance probe, a resistance probe, an ultrasonic sensor, an optical sensor, a mechanical float, a pressure sensor for example that enables autonomous or local and/or remote display of hydration values, for example to enable the container cap to display hydration usage and/or requirements for maintaining hydration locally or via a mobile device such as a phone if connected wirelessly or both locally and on the mobile device.

Known beverage containers are not directly capable of actively ensuring that proper hydration levels are maintained for a user. Existing containers merely dispense liquid when the user decides to drink as known beverage containers are incapable of taking time, weight, age, humidity, temperature, activity levels, motion, altitude, medical needs or any other inputs into account to actively prompt the user to drink. Once a user senses thirst, the user is usually already dehydrated. Performance of the user thus decreases and in situations such as diabetes, the amount of insulin required increases. Hence, keeping the user hydrated may actually reduce the amount of drugs needed by the user as the human body may be better able to utilize drugs when properly hydrated. There are no known systems that interface with a Service Center to provide information related to the hydration of an individual, for example pre or post surgery.

For at least the limitations described above, there is a need for fluid consumption monitoring system for a beverage container that can be carried by hand or securely attached to a belt, garment, or bag, with a simple, reliable flexible seal valve. In addition, there is a need for a cap equipped with various sensors and output devices that provide a wide range of useful information to the user and prompt the user to consume liquid based on a number of factors including time, weight, age, humidity, temperature, activity levels, motion, altitude, medical needs.

BRIEF SUMMARY OF THE INVENTION

One or more embodiments of the invention are related to a fluid consumption monitoring system for example that includes a probe or sensor that may extend into the container, or a weight measuring sensor that measures or otherwise calculates the quantity of fluid in the container, or a tilt meter or inclinometer that indirectly estimates the amount of fluid dispensed from the container. Such a device, in at least one embodiment, may measure the fluid level using a capacitance probe, a resistance probe, an ultrasonic sensor, an optical sensor, a mechanical float, a pressure sensor, or any other technique for use with a beverage container, including estimating the amount of fluid dispensed by calculating the tilt, timing the tilt and calculating the amount of fluid dispensed through a predetermined size hole in the top of the container. In at least one embodiment, the system includes a cap that couples with a beverage container, a processor coupled with the cap, at least one activity level sensor coupled with the processor, such as an inclinometer (or other position or orientation sensor), and/or an accelerometer/gyro or wireless interface, and a timer coupled with the processor. In some embodiments, an inclinometer may be utilized to estimate both volume dispensed and activity levels in a low cost configuration compared to impeller based systems that are expensive and hard to clean. Embodiments may communicate over the wireless interface with an external device such as a mobile phone, tablet or other computer, such as a FITBIT® or other user movement or activity sensor to receive and transmit information from and to respectively. Embodiments may display hydration related values local to the apparatus, for example with LED's on the cap, or if a wireless device is attached, display the hydration values on the cap, or display the hydration values both on the cap and on the wireless device. If the apparatus is in autonomous mode, data saved while no wireless connection is available may be sent to the wireless device when connected at a later time. If the embodiment of the invention includes a display, then the data may be locally displayed or if not saved and displayed when the wireless connection is established with the remote device for example.

In one or more embodiments, the at least one activity level sensor or inclinometer may detect at least one tilt angle of the beverage container when the beverage container is tilted. Any other type of sensor such as contact sensors or Reed switch type sensors may be utilized to estimate or otherwise detect tilt and infer activity and volume of liquid dispensed. In at least one embodiment, when the beverage container is tilted at the at least one tilt angle, the timer may measure an amount of time the beverage container is tilted. In one or more embodiments, the processor may determine a volume of fluid dispensed from the beverage container based on the at least one tilt angle and the amount of time the beverage container is tilted, for example in combination with a button press and/or other sensors that detect if liquid is actually flowing through the system. Embodiments of the activity level sensor or inclinometer may be sampled or otherwise queried over time to determine when the cap has tilted over time, which may be indicative of activity. In one or more embodiments using simply open/close tilt sensors, if a predefined number of open/close signals is received per unit time, then this signal may be indicative of a series of steps. If the number of open/close signals is too high or too low versus predefined limits, then the signals may be eliminated as false positive steps.

In one or more embodiments the activity level sensor or inclinometer may thus provide activity detection and volume sensing that traditionally has required relatively expensive GPS or accelerometers for activity sensing and relatively expensive flow meters for detecting dispensed volume. Thus embodiments of the invention may utilize one component to perform two functions and thus replace two expensive components typically utilized in the art.

By way of at least one embodiment, the system may include a button including at least one arm, and a flexible seal valve including a slit. In one or more embodiments, the cap is moveably coupled with the button. In at least one embodiment, the flexible seal valve is coupled with the cap. In one or more embodiments, the at least one arm is coupled with the flexible seal valve to operatively open and close the slit in the flexible seal valve when the button is moved in a first and second direction respectively.

According to at least one embodiment, the system may include a handle rotatably coupled with the cap. In one or more embodiments, the handle may move from a first closed position on a front end of the cap to a second carrying position, and may move to a third open position on a back end of the cap, wherein the back end is on an opposite end of the cap relative to the front end. In at least one embodiment of the invention, in the first closed position the handle may move to operatively cover the slit in the flexible seal valve, to keep the slit and/or valve clean, for example when in a gym bag. In at least one embodiment, in the second carrying position and the third open position, the handle may uncover the slit.

By way of one or more embodiments, the system may include a button, wherein the cap may include a base element and top element coupled with the flexible seal valve, and wherein the top element covers the button and at least a portion of the flexible seal valve. In at least one embodiment of the invention, the button may slide in and out of one or more of the top element and the base element. In one or more embodiments, the top element may include a hole that the flexible seal valve is situated within.

In at least one embodiment, the at least one arm may include a wishbone shaped arm that extends from a horizontal orientation to a perpendicular orientation, such that the at least one arm is attached on an opposing side of the flexible seal valve in order to pull open and closed the slit to open and close the flexible seal valve.

In one or more embodiments, the system may include a clip element, and wherein the base element may include a base element outer surface, such that the clip element may attach to the base element on the base element outer surface. In at least one embodiment, the base element may include a first partially enclosed inner portion and the top element may include a second partially enclosed inner portion. In one or more embodiments, the flexible seal valve may extend through and couple with the base element via the first partially enclosed inner portion and may extend through and couple with the top element via the second partially enclosed inner portion. The clip element may include a weight measuring sensor between the container and clip or in other embodiments the cap itself may include a weight measuring sensor to calculate the amount of liquid in the container based on the difference of weight in the empty and full container as described further below.

According to one or more embodiments, the top element may include one or more of a top element outer surface and at least one compartment formed on the top element outer surface, and at least one electronic element situated in the at least one compartment. In at least one embodiment, the cap may include at least one display device, wherein the processor may indicate on the at least one display device the volume of fluid dispensed from the beverage container, and/or indicate when to drink and/or how much to drink. In one or more embodiments, the system may include at least one activity level input that obtains at least one activity level of a user of the beverage container to determine an amount of fluid a user of the beverage container should consume and may indicate the amount of fluid on the at least one display device. Alternatively, or in combination the apparatus may interface to any external user tracking device such as a mobile device or cell phone with an accelerometer, or a FITBIT® user movement measurement device to obtain activity level, calories burned, activity duration and intensity, temperature, heart rate or any other value that the mobile device, cell phone or FITBIT® user measurement device can sense. After obtaining the activity level, calories burned, activity duration and intensity, temperature, heart rate, the apparatus may alter the amount of fluid that is recommended for user intake based on these values.

In at least one embodiment, the system may include at least one sensor that senses one or more signals. In one or more embodiments, the at least one sensor may include at least one activity level input sensor that measures the at least one activity level based on motion of a user of the beverage container to determine an amount of fluid a user of the beverage container should consume and may indicate the amount of fluid on the at least one display device.

In one or more embodiments, the at least one sensor may include at least one thermometer that measures an external temperature, such that the at least one display device may indicate an amount of fluid a user of the beverage container should consume based on the external temperature. In at least one embodiment, the at least one sensor may include the at least one activity level input and the at least one thermometer.

In one or more embodiments, the at least one sensor may include at least one weight sensor coupled between the clip element and the base element, or coupled between the handle and the top element, or in any other location with respect to the container. In at least one embodiment, the processor may determine a weight of the beverage container to determine an amount of fluid a user of the beverage container has consumed based on the weight, such as from the at least one weight sensor, and may indicate the amount of fluid that should be consumed based on the weight on the at least one display device. In one or more embodiments, the processor may accept a weight of a user of the beverage container to determine an amount of fluid a user of the beverage container should consume based on the weight, and may indicate the amount of fluid that should be consumed on the at least one display device.

By way of at least one embodiment, the at least one electronic device may include at least one communication device that communicates with at least one external device to relay one or more signals. In one or more embodiments, the at least one communication device may accept information from the external device to determine an amount of fluid a user of the beverage container should consume based on an age of the user, weight of the user, temperature, humidity, sunny or cloudy value, activity level, time of day or time since last drink, activity level, motion, altitude, medical needs, number of steps, heart rate, respiration rate, blood pressure, blood oxygen level, hydration value obtain from the user, or any combination thereof.

In at least one embodiment of the invention, the at least one electronic device may include a start button and a timer. In one or more embodiments, the at least one display device may include at least one light-emitting diode (LED) coupled with the timer and the at least one sensor, wherein the at least one LED may flash to indicate one or more time periods to consume the fluid as determined by the timer and whether enough fluid has been consumed by the user as determined by the at least one sensor. The at least one LED may display information if there is no wireless connection or optionally not display information locally and send the information to a connected wireless mobile device. This may be performed to save power for example. Other embodiments enable display on both the at least one LED and mobile device concurrently. In at least one embodiment data may be saved on the apparatus until a wireless device is connected, at which point the data is uploaded to the mobile device for analysis and/or display for example.

In at least one embodiment, the at least one LED may remain to flash until enough fluid has been consumed by the user at the one or more time periods as determined by the timer and the at least one sensor. In one or more embodiments, the start button may be pressed to restart the timer to determine the one or more time periods. Operation of the LED's may also be controlled from the mobile device when connected and for example synchronized so that the display on the mobile device matches the display on the apparatus.

According to at least one embodiment, the at least one LED may flash to indicate the time to consume a first amount of the fluid at a first time period of the one or more time periods, and may remain to flash until the first amount of the fluid has been consumed by the user. In one or more embodiments, after a pre-determined amount of time after the first amount of fluid has been consumed, the at least one LED may flash to indicate the time to consume a second amount of the fluid at a second time period after the first time period, and may remain to flash until the second amount of the fluid has been consumed by the user. Alternatively, or in combination, the apparatus may send a wireless message to a mobile device, cell phone or user movement sensor to display a message indicating a time to drink or for any other information, or obtain any information as well.

By way of one or more embodiments, the at least one electronic device may include one or more of the start button, the timer and at least one sound emitting device coupled with the timer and the at least one sensor. In at least one embodiment of the invention, the at least one sound emitting device may beep to indicate one or more time periods to consume the fluid as determined by the timer, and whether enough fluid has been consumed by the user as determined by the at least one sensor. In one or more embodiments, the at least one sound emitting device may remain to beep until enough fluid has been consumed by the user at the one or more time periods as determined by the timer and the at least one sensor. In at least one embodiment, the start button may be pressed to restart the timer to determine the one or more time periods.

According to at least one embodiment, the at least one sound emitting device may beep to indicate the time to consume a first amount of the fluid at a first time period of the one or more time periods and may remain to beep until the first amount of the fluid has been consumed by the user. In one or more embodiments, after a pre-determined amount of time after the first amount of fluid has been consumed, the at least one sound emitting device may beep to indicate the time to consume a second amount of the fluid at a second time period after the first time period and may remain to beep until the second amount of the fluid has been consumed by the user.

At least one embodiment of the invention may include the at least one sound emitting device coupled with the timer and the at least one sensor, and at least one LED. In at least one embodiment, the at least one sound emitting device and the at least one LED may operate and function simultaneously. In one or more embodiments, the at least one LED may flash and the at least one sound emitting device may beep to indicate the one or more time periods to consume the fluid as determined by the timer, to indicate whether enough fluid has been consumed by the user as determined by the at least one sensor, and to indicate the time to consume the first amount of the fluid at the first time period of the one or more time periods, and may remain to flash and beep until the first amount of the fluid has been consumed by the user as determined by the timer and the at least one sensor. In at least one embodiment, after the pre-determined amount of time after the first amount of fluid has been consumed, the at least one LED may flash and the at least one sound emitting device may beeps to indicate the time to consume the second amount of the fluid at the second time period after the first time period, and may remain to flash and beep until the second amount of the fluid has been consumed by the user. The at least one sound emitting device may include sound output devices on the apparatus and/or mobile device.

BRIEF DESCRIPTION OF THE DRAWINGS

The above and other aspects, features and advantages of at least one embodiment of the invention will be more apparent from the following more particular description thereof, presented in conjunction with the following drawings wherein:

FIG. 3A is perspective view of an exemplary embodiment of a container cap in accordance with an embodiment of the invention.

FIG. 3B is an alternate perspective view of an exemplary embodiment of a container cap in accordance with an embodiment of the invention.

FIG. 3C is a top view of an exemplary embodiment of a container cap in accordance with an embodiment of the invention.

FIG. 3D is a side view of an exemplary embodiment of a container cap in accordance with an embodiment of the invention.

FIG. 3E is a front view of an exemplary embodiment of a container cap in accordance with an embodiment of the invention.

DETAILED DESCRIPTION OF THE INVENTION

The following description is of the best mode presently contemplated for carrying out at least one embodiment of the invention. This description is not to be taken in a limiting sense, but is made merely for the purpose of describing the general principles of the invention. The scope of the invention should be determined with reference to the claims.

Figure 1:
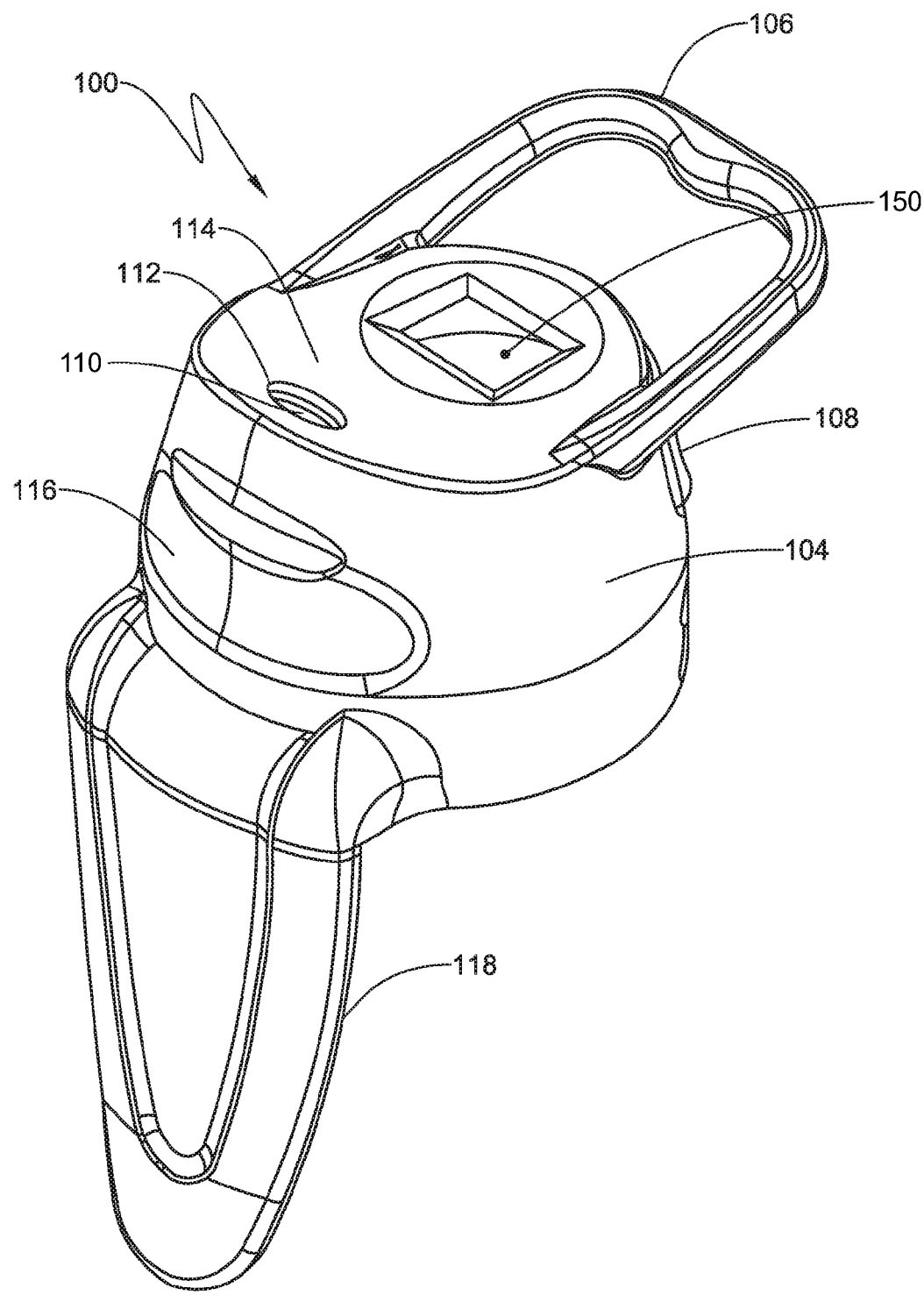
FIG. 1 is a perspective view showing an exemplary embodiment of the beverage container cap described herein.

FIG. 1 is a perspective view showing an exemplary embodiment of the fluid consumption monitoring system described herein. As shown in FIG. 1, at least one embodiment of the invention includes a cap 100 that attaches to a beverage container by means of threads 102 (see FIG. 4C) that engage complimentary threads on the beverage container. It will be understood that other systems and structures may be used to attach the cap to the beverage container, such as elastomeric seals, snap fit connections, etc., in one or more embodiments of the invention, such as any suitable attachment that provides a secure, fluid-tight seal between the beverage container and cap. In at least one embodiment, cap 100 may be used with any type of beverage container having any shape, configuration, or construction and including without limitation steel and plastic water bottles, coffee and other insulated cups, etc., or any combination thereof.

In various exemplary embodiments, cap 100 may include a housing 104 that connects to the beverage container and that may be made from a single piece or assembled from two or more component parts. Housing 104, in at least one embodiment, may include a handle 106 extending outward from the housing to allow the user to easily carry the beverage container by hooking it through one or more fingers or by attaching it to a garment or bag by a hook or other connector such as a carabiner. Housing 104, in one or more embodiments, may also include a valve button 108 that may be actuated by pressing it inward relative to the outer surface of the housing 104 to open a valve 110 and allow the beverage or fluid in the container to flow out of the opening 112. In various exemplary embodiments, handle 106 extends from the housing 104 at a location above and adjacent to the valve button 108 to provide a stable structure for the user's hand to securely grasp the beverage container and cap 100 when the valve button 108 is actuated.

In at least one embodiment, the beverage in the container attached to the cap 100 flows from opening 112 when valve 110 is opened. In an exemplary embodiment of the invention, opening 112 is located near the periphery of a top surface 114 of the housing 104. In one or more embodiments, top surface 114 may take any shape and may be contoured to manage the flow of liquids that escape from the opening 112. In at least one embodiment as shown in the accompanying drawings, top surface 114 may be sloped back and away from opening 112 and slightly down to the sides to prevent accumulation of fluids, and to direct the flow of any fluids that leak from the opening 112 away from the user. By positioning the opening as shown on the top surface 114, in one or more embodiments, the taper and angle provide for a proper mouth fit for easy drinking, with no place for fluids to collect.

In at least one embodiment of the invention, valve button 108 may be located on a side surface of the housing 104. Valve button 108 may be actuated by the user by depressing it inwardly relative to the side surface of housing 104, according to one or more embodiments. As shown in the accompanying drawings, in an exemplary embodiment of the invention, the valve button 108 may be located on the side surface of housing 104 generally opposite the peripheral location of opening 112. In this location, in at least one embodiment, one or more of the user's fingers will naturally land on the valve button 108 when the beverage container is grasped and raised to the user's mouth. By way of at least one embodiment, handle 106 may be arranged such that the user's finger will naturally be positioned on the valve button 108 when the user grasps the beverage container. In various exemplary embodiments, handle 106 extends out and up from the edge of the top surface 114 of the housing 104 at a location above and adjacent to the valve button 108 at an angle of 15-25 degrees from a horizontal plane. This location and upward angle, according to one or more embodiments, allows for a comfortable, secure grip that naturally places the user's index finger directly on the valve button 108 such that the valve may be operated while maintaining a secure grip on the beverage container.

By way of at least one embodiment, valve button 108 may be contoured to naturally engage the user's finger so that it may easily be depressed by pressure from the user's finger. Housing 104 may also include a gripping area 116 on the side surface of housing 104 adjacent to opening 112, in one or more embodiments, where the user's thumb will naturally land when the beverage container is grasped for use. In at least one embodiment of the invention, gripping area 116 may be contoured or provided with a surface that improves frictional engagement by the user's thumb.

In at least one embodiment of the invention, housing 104 may include a clip 118 that extends downward from lower periphery of housing 104 and may be slipped over a belt or other strap, or into a pocket on a garment or bag to securely hold the beverage container. In one or more embodiments, clip 118 may be contoured to improve engagement with such structures. In at least one embodiment, the inner surface of clip 118 may be concave to provide for secure engagement when used with a belt or in a pocket. Some or all of clip 118 may also be contoured or may be comprised of a material that improves frictional engagement, in one or more embodiments, such as an elastomeric material or coating.

Figure 2B:
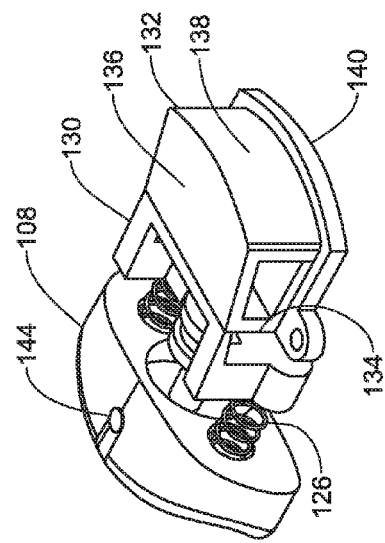
FIG. 2B is perspective view of an exemplary embodiment of a valve button, actuator and valve sealing mechanism in accordance with an embodiment of the invention.
Figure 2C:
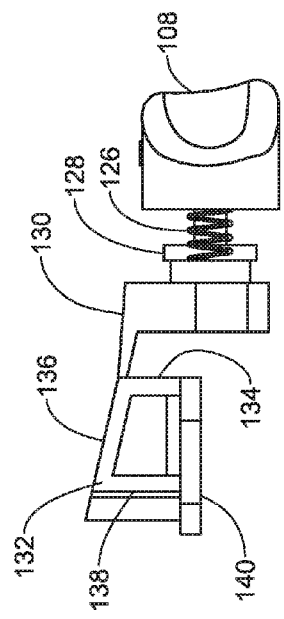
FIG. 2C is side view of an exemplary embodiment of a valve button, actuator and valve sealing mechanism in accordance with an embodiment of the invention.
Figure 2A:
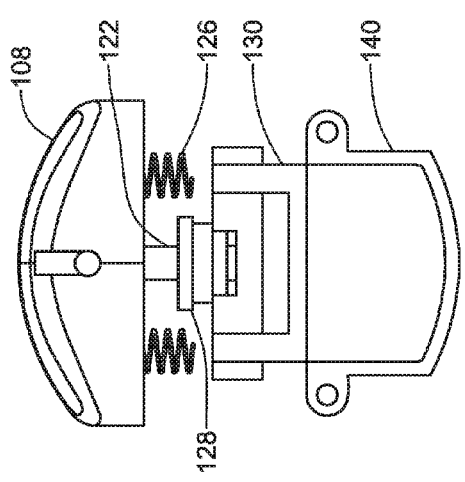
FIG. 2A is top view of an exemplary embodiment of a valve button, actuator and valve sealing mechanism in accordance with an embodiment of the invention.

FIG. 2A is top view of an exemplary embodiment of a valve button, actuator and valve sealing mechanism in accordance with an embodiment of the invention. In an exemplary embodiment of the invention, valve button 108 may be depressed into a valve button cavity 120 extending into the housing 104. In one or more embodiments, valve button 108 may include a valve button shaft 122 or other extension that extends through an aperture 124 in the valve button cavity 120 into the interior of housing 104. In at least one embodiment, valve button 108 may be biased outward by springs 126 or any other suitable biasing mechanism. In at least one embodiment of the invention, a button shaft seal 128 seals the aperture 124 and may retain the valve button shaft 122 to retain the valve button 108 in the valve button cavity 120. In various embodiments, other mechanisms such as elastomeric seals or molded stops may be use to retain the valve button 108 in the valve button cavity 120.

In at least one embodiment of the invention, valve button shaft 122 may be attached to a valve seal actuator 130. The valve seal actuator 130, in one or more embodiments, may be located inside housing 104, and in its resting position may be adjacent to the valve button cavity 120. In at least one embodiment, the valve seal actuator 130 may help retain the valve button 108 in the valve button cavity 120.

Figure 2D:
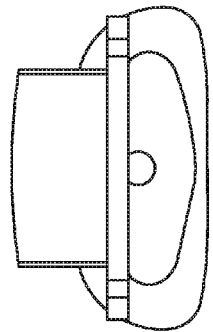
FIG. 2D is front view of an exemplary embodiment of a valve button, actuator and valve sealing mechanism in accordance with an embodiment of the invention.

FIG. 2B is perspective view of an exemplary embodiment of a valve button, actuator and valve sealing mechanism in accordance with an embodiment of the invention and FIG. 2D is front view of an exemplary embodiment of a valve button, actuator and valve sealing mechanism in accordance with an embodiment of the invention. In various exemplary embodiments of the invention, as shown in FIGS. 2B and 2D, valve seal 132 may include an elastomeric material that is preferably a food-grade material such as silicone. Other elastomeric materials such as thermoplastic elastomers or similar materials that can maintain their shape over time may also be appropriate according to at least one embodiment of the invention. In one or more embodiments, valve seal 132 may take any suitable shape and be placed in a suitable location that allows it to be retained within housing 104 in a resting position where it seals off fluid flow from opening 112. In various exemplary embodiments of the invention, valve seal 132 may be slightly loaded such that it is biased against the internal top surface of the housing 104 in the region of the opening 112 to seal the opening 112. By mounting the valve seal 132 under a slight load, in at least one embodiment, the valve seal 132 uses the spring force of the elastomer itself to achieve and maintain a seal, thus eliminating the need for a separate biasing mechanism.

FIG. 2C is side view of an exemplary embodiment of a valve button, actuator and valve sealing mechanism in accordance with an embodiment of the invention. In at least one embodiment of the invention, valve seal 132 may include a generally U-shaped profile with a generally vertical actuating side 134, a sealing side 136 that matches the interior contours of the housing 104 in the area of opening 112, and a generally vertical anchor side 138 that may be contoured to match the shape of the interior side of the housing 104 or other adjacent surface. In one or more embodiments, the actuating side 134 may be disposed toward the interior of the housing 104 and the anchor side 138 may be adjacent to the housing 104 or another surface or feature that maintains the anchor side in a fixed position. At rest, according to at least one embodiment of the invention, the sealing side 136 is in contact with inner side of the top surface 114 of the housing 104 and may be under a slight load such that it completely covers and seals the opening 112. In at least one embodiment, a seal mounting plate 140 may be affixed to housing 104 and the valve seal 132 may be seated in the seal mounting plate 140, holding the valve seal 132 in position within the housing 104. In an exemplary embodiment of the invention, an appropriate load on the valve seal 132 may be achieved by positioning seal mounting plate 140 relative to the interior of top surface 114 of housing 104 so that the valve seal 132 is compressed in the range of 20 to 30 thousandths of an inch.

In various exemplary embodiments of the invention, the valve seal 132 seals the opening 112 in the resting position and may be deformed by a force exerted by valve actuator 130 such that it no longer seals the opening 112.

FIG. 3A is perspective view of a container cap, FIG. 3B is an alternate perspective view of a container cap, FIG. 3C is a top view of a container cap, FIG. 3D is a side view of a container cap, and FIG. 3E is a front view of a container cap, in accordance with one or more embodiments of the invention.

Figure 4A:
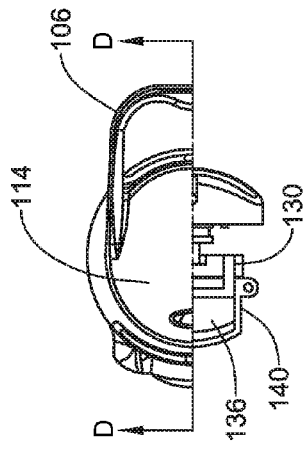
FIG. 4A is a top view of an exemplary embodiment of a container cap in accordance with an embodiment of the invention.
Figure 4B:
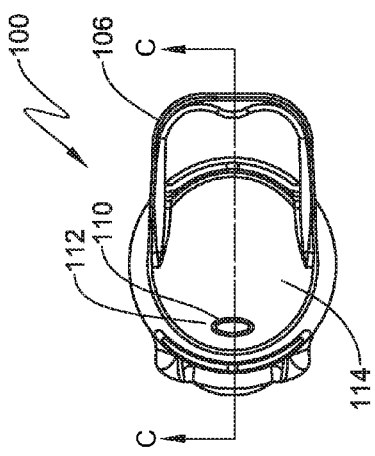
FIG. 4B is a partial section top view of an exemplary embodiment of a container cap in accordance with an embodiment of the invention.
Figure 4C:
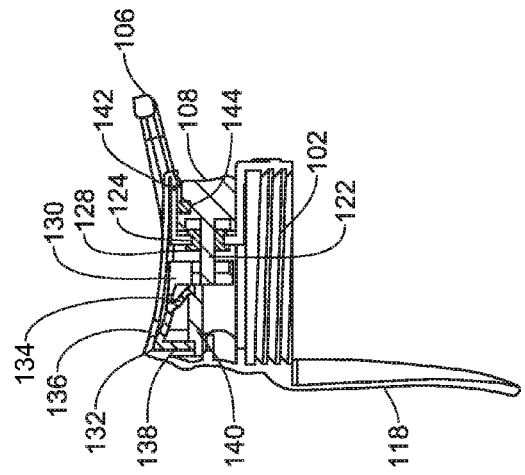
FIG. 4C is a section C-C side view of an exemplary embodiment of a container cap in accordance with an embodiment of the invention with the valve closed.
Figure 4D:
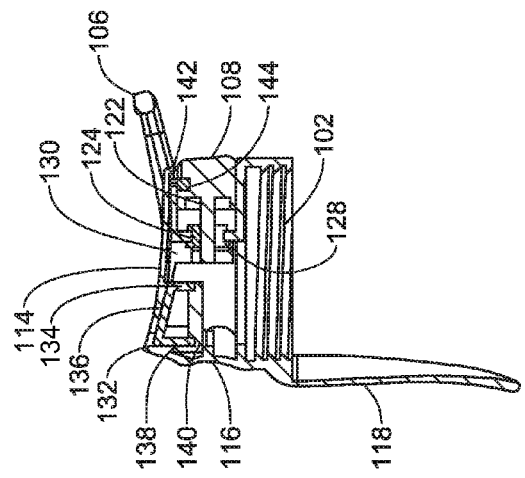
FIG. 4D is a section D-D side view of an exemplary embodiment of a container cap in accordance with an embodiment of the invention with the valve open.

FIG. 4A is a top view of a container cap, FIG. 4B is a partial section top view of a container cap, FIG. 4C is a section C-C side view of a container cap in accordance with an embodiment of the invention with the valve closed, and FIG. 4D is a section D-D side view of a container cap with the valve open, in accordance with one or more embodiments of the invention.

Referring to valve sections C-C (closed) and D-D (open), as shown in FIGS. 4C and 4D, in at least one embodiment of the invention, when the valve button 108 is depressed into the valve button cavity 120, valve actuator 130 is forced in a lateral direction such that a portion of the valve actuator 130 exerts a force on the actuating side 134 of the valve seal 132. In one or more embodiments, this force on the actuating side 134 of the valve seal 132 causes the valve seal 132 to elastically deform away from the opening 112. As long as a fluid path is maintained from the beverage container through the housing 104 to the opening 112, according to at least one embodiment, the beverage may be dispensed through opening 112.

By way of one or more embodiment, the valve actuator 130 may include a wide range of geometries to allow for a fluid path through the housing 104 to the opening 112. In at least one embodiment of the invention, valve actuator 130 includes a main body that extends in a generally vertical direction and is attached to the valve button shaft 122 such that it moves in a lateral direction when the valve button 108 is pressed by the user. In one or more embodiments, the valve actuator may include a generally U-shaped section that extends laterally to a point adjacent to or in contact with the valve seal 132 on the upper portion of the actuating side 134 in the resting position with the valve closed. In at least one embodiment, a large aperture may extend through the valve actuator 130 below and the in the area of the generally U-shaped lateral extension, which allows fluid to easily pass through the valve actuator. When the valve button 108 is pressed by the user, by way of at least one embodiment, the valve actuator 130 may move laterally such that the generally U-shaped lateral extension exerts a lateral force on the upper portion of the actuating side 134 of the valve seal 132, deforming the valve seal 132 to overcome the sealing bias, and separating the sealing side 136 from the inner surface of the top of the housing 104 and opening 112. As such, in one or more embodiments, the opening 112 is then open to fluid flowing from the beverage container through the aperture in the valve actuator 130.

It will be readily understood by those skilled in the art that the arrangement and geometries of the various valve components described herein according to one or more embodiments of the invention may be varied to achieve the same result of a deformable, elastomeric valve seal. For example, in at least one embodiment of the invention, the geometry and mounting of the valve seal 132 may be changed in a variety of ways that still use the spring force of the elastomer itself to achieve and maintain a seal. Similarly, in one or more embodiments, the geometry and mounting of the valve actuator 130 may be changed in a variety of ways that achieve the necessary deformation of the valve seal 132 while allowing a fluid path from the beverage container to the opening 112 when the valve is open.

In various exemplary embodiments of the invention, the valve button cavity 120 may be sealed such that the valve button 108 and the biasing springs 126 or other button biasing mechanism do not come in contact with the contents of the beverage container and are kept clean and dry. Because the exposed parts disposed within the interior of the housing 104 are firmly attached and made of a suitable elastomer or other durable material, by way of at least one embodiment, this allows the entire cap 100 to be completely immersed in water for cleaning by hand or in a dishwashing machine. The simplicity of the design in one or more embodiments allows for the cap to be made so that it is microwave safe.

Figure 5:
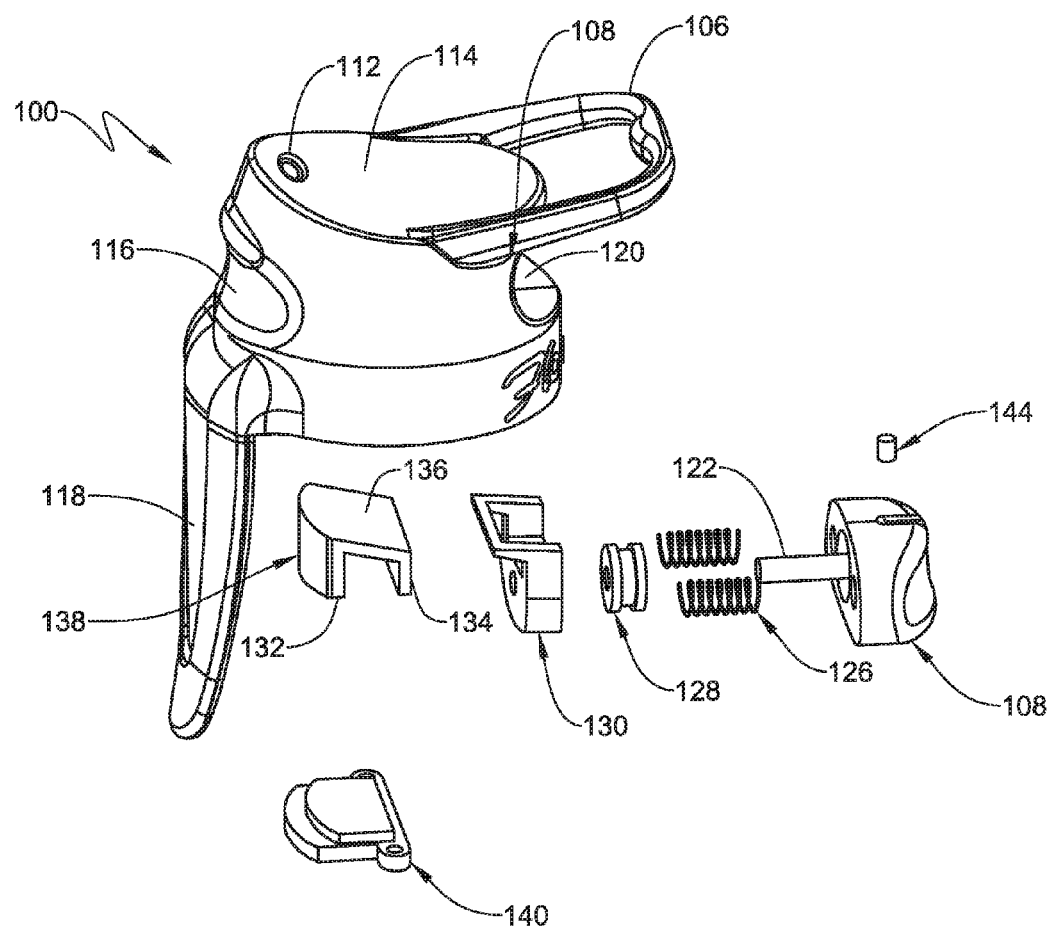
FIG. 5 is an exploded view of an exemplary embodiment of a container cap in accordance with an embodiment of the invention.

FIG. 5 is an exploded view of an exemplary embodiment of a container cap in accordance with an embodiment of the invention. In various exemplary embodiments, an air vent may be provided in the housing 104 to provide for free fluid flow through the opening 112. In at least one embodiment, an air vent 142 may be located in button cavity 120 and may be provided with an air vent seal 144 to prevent the unintentional release of fluids from the air vent 142. In one or more embodiment, this location improves the aesthetics of the beverage cap by placing the air vent 142 in a location where it cannot be seen. In an exemplary embodiment of the invention, air vent seal 144 may be affixed to valve button 108 and positioned such that it seals the air vent 142 in the resting position when the valve is closed, but then moves laterally such that the air vent 142 is open when the valve button 108 is pressed by the user and the valve is opened. In this arrangement, in at least one embodiment, the air vent seal 144 and the valve seal 132 may be both actuated by pressure on the valve button 108, wherein both are actuated simultaneously such that the fluid may flow freely to the opening 112.

Figure 6:
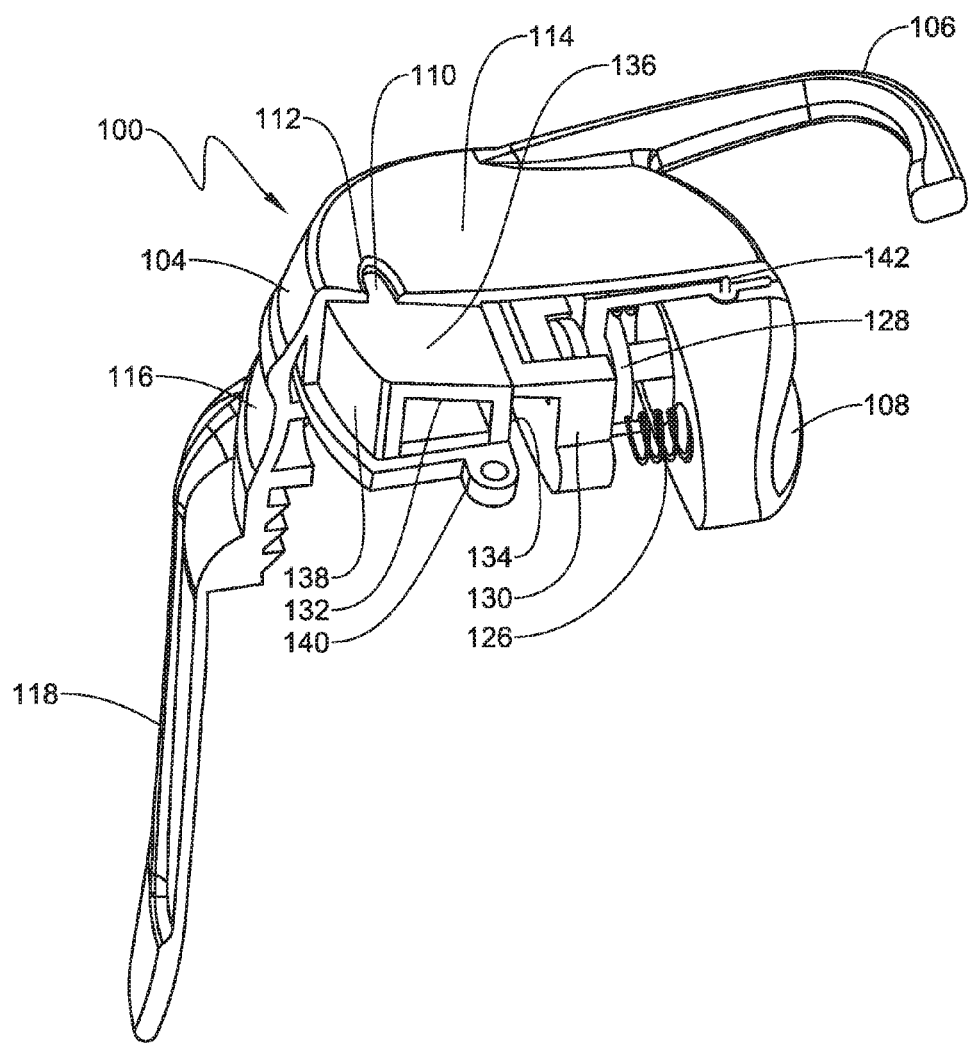
FIG. 6 is a perspective partial section view of an exemplary embodiment of a container cap in accordance with an embodiment of the invention.

FIG. 6 is a perspective partial section view of an exemplary embodiment of a container cap in accordance with an embodiment of the invention. In various exemplary embodiments, the housing 104 may include a cavity 150 to mount decorative items, instruments such as a compass or altimeter, or informational devices such as display screens. In various exemplary embodiments of the invention, the beverage container cap may be equipped with one or more digital processors, storage devices, output devices, sensors, accelerometers, gyroscopes, GPS systems, pedometers, physiological monitors, thermometers, etc. that provide information that may be output to the user via a display mounted in cavity 150. In at least one embodiment, sensors may be placed at appropriate locations throughout the housing including the valve button 108 and gripping area 116 where the user's hands naturally grip the cap during use. In one or more embodiments, systems including sensors and processors may be provided to measure, store, and display instantly or over time the user's heart rate, respiration rate, blood pressure, blood oxygen level, hydration or any other physiological characteristics. In at least one embodiment, such systems may also be provided to measure, calculate, store, and display instantly or over time trip, location, and activity information such as physical location, temperature, humidity, barometric pressure, time, elapsed time, number of steps, alarms, altitude, etc.

Figure 7:
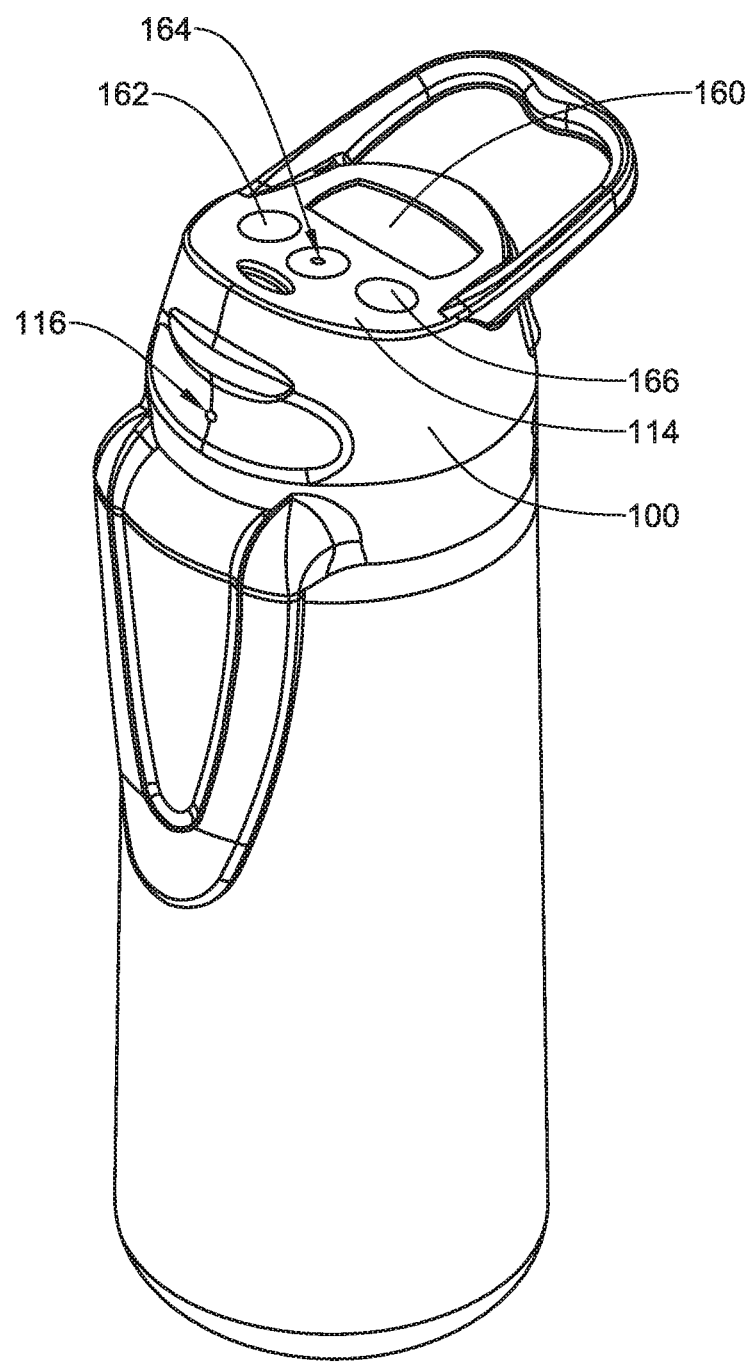
FIG. 7 is a perspective view of an exemplary embodiment of a container cap in accordance with an embodiment of the invention attached to a bottle.

FIG. 7 is a perspective view of an exemplary embodiment of a container cap in accordance with an embodiment of the invention attached to a bottle. As shown in FIG. 7, in various exemplary embodiments of the invention, the cap 100 may be fitted with a display device 160 such as an LCD screen to display information to the user. Where an appropriate cavity 150 is provided, in at least one embodiment, the screen may be positioned on the top surface 114 of the cap 100 such that it may easily be seen by the user. In one or more embodiments, various controls may be positioned at appropriate locations on the cap 100 to select the information to be displayed on display device 160. In various exemplary embodiments, control buttons 162, 164, 166, may be provided, or the display screen 160 may be a touchscreen with controls that are activated by the user's touch or gesture.

In various exemplary embodiments of the invention, digital storage, processing, and communications may be provided to manage data collected by such systems. Communications such as one or more of Bluetooth, WiFi, WAN, NFC, cellular, etc., by way of at least one embodiment, allow the system to communicate with smartphones, laptops, networks, cloud-based systems, etc., or a combination thereof, to transfer, exchange, or receive information for storage or display to the user. One or more embodiments may include a wired plug for recharging if desired and for communications, or may communicate wirelessly and utilize disposable batteries to power the various components. Such systems, in one or more embodiments, allow the user to transfer information gathered during their activities for storage and use without the need to carry any additional electronic devices. For example, in at least one embodiment, a cap may include one or more sensors that gather basic physical information such as one or more of heart rate, respiration rate, blood pressure, blood oxygen level and hydration levels. This information, in at least one embodiment, may be stored and/or displayed to the user via a display device 160 located in cavity 150, and transferred to a remote system for one or more of storage, compilation, analysis and display on a different device such as a smartphone, tablet, or other computer, e.g., a user measurement device such as a FITBIT®, or any combination thereof (see FIG. 18). The system, in one or more embodiments, may be controlled by any appropriate user interface mounted in the housing such as a touchscreen, buttons, or other user input devices, or any combination thereof.

Figure 8B:
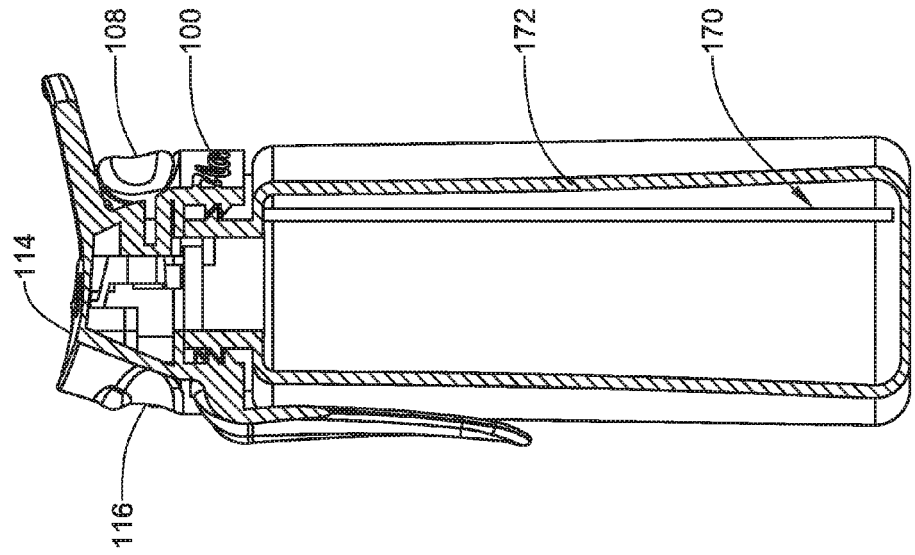
FIG. 8B is a section B-B view of an exemplary embodiment of a container cap in accordance with an embodiment of the invention attached to a bottle.
Figure 8A:
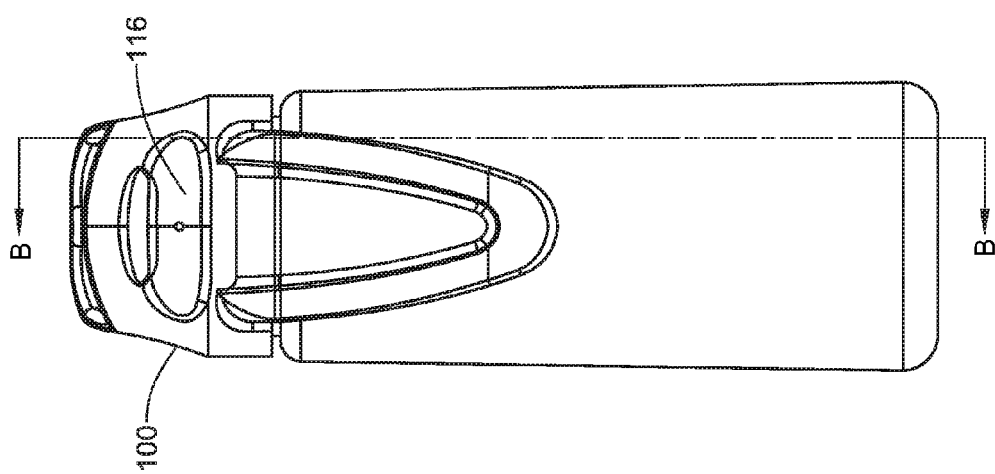
FIG. 8A is a front view of an exemplary embodiment of a container cap in accordance with an embodiment of the invention attached to a bottle.

FIG. 8A is a front view of a container cap attached to a bottle, and FIG. 8B is a section B-B view a container cap attached to a bottle, according to one or more embodiments of the invention. As discussed above, in one or more embodiments, a wide range of different sensors may be used to gather information relevant to the user. In various exemplary embodiments, a probe 170 or sensor may extend into the container 172 that measures the quantity of fluid in the container 172. Such a device, in at least one embodiment, may measure the fluid level using a capacitance probe, a resistance probe, an ultrasonic sensor, an optical sensor, a mechanical float, a pressure sensor, or any other technique. One or more embodiments of the invention include a processor that may then use the fluid level measurement to determine the quantity of fluid that has been consumed over time. In at least one embodiment, the system may then display the quantity of fluid consumed by the user on display device 160. In one or more embodiments, the probe may extend from the cap into the container 172, or may be built-in or attached directly to the container 172, and may feed data to the cap or device for display to the user.

Figure 9:
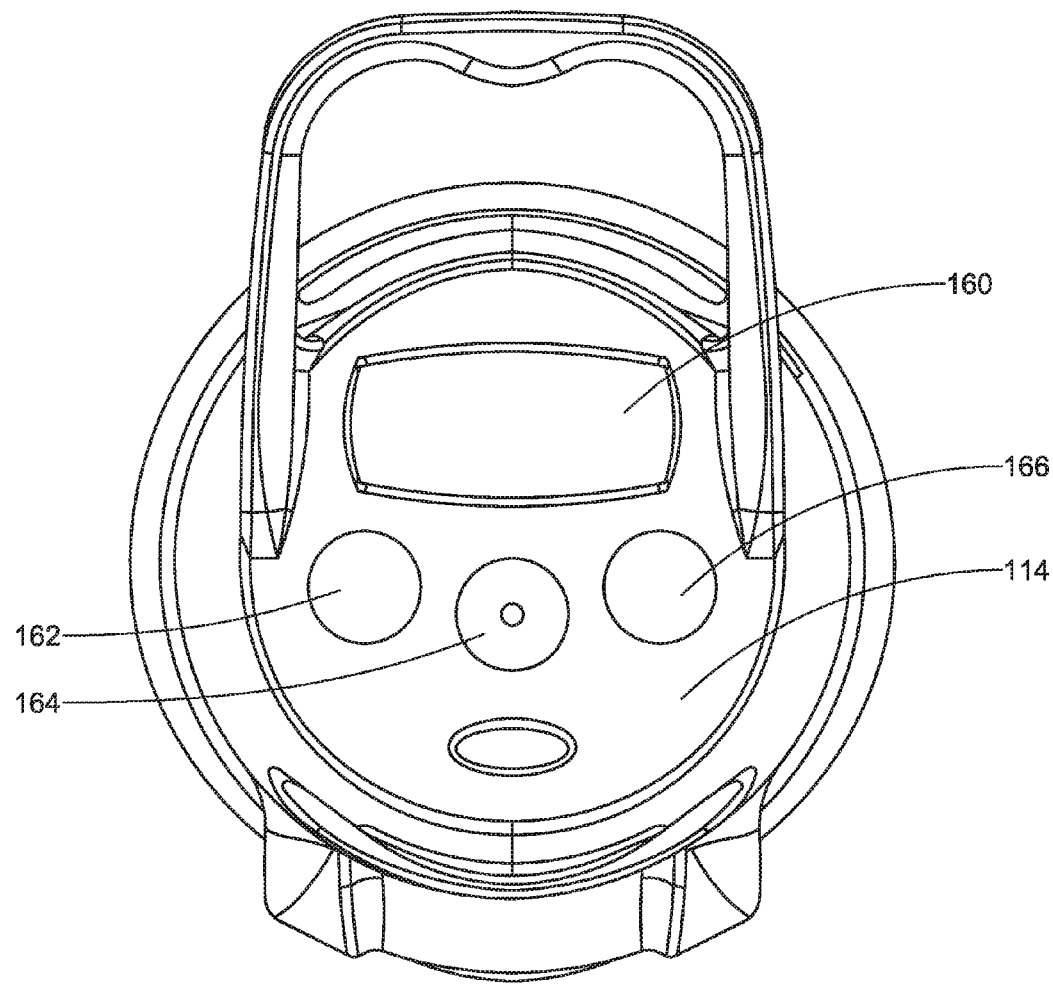
FIG. 9 is a top view of an exemplary embodiment of a container cap in accordance with an embodiment of the invention.

FIG. 9 is a top view of an exemplary embodiment of a container cap in accordance with an embodiment of the invention. In at least one embodiment, the user's heart rate may be measured and displayed to the user on display device 160. In one or more embodiments, the heart rate may be detected by measuring electrical signals between two locations on the users body, such as between the two hands or between one hand and another part of the body, between two fingers, or even between two points on one finger. In at least one embodiment, the heart rate may be detected using one or more optical sensors that measure the relative amount of light transmitted through a finger or thumb, or by any other technique that may be developed. In one or more embodiments, heart rate sensor electrodes may be provided on the valve button 108 and gripping area 116 where the user's hands naturally grip the cap during use, or on one or more of the control buttons 162, 164, 166, or at any other locations on the cap 100 or container 172.

By way of at least one embodiment, the user's step count may similarly be measured and displayed to the user on the display device 160. Step count may be measured using an electronic sensor of any type, including an accelerometer, or inclinometer, or contact switch that detects movement mechanically, such as using a weighted spring that contacts a switch, flexes a piezo-membrane, or flexes a strain gauge, a vibration sensor, or by any other suitable means in the cap 100 or container 172, according to at least one embodiment of the invention. One or more embodiments may obtain the step count wirelessly and/or correlate and/or calibrate the internally calculated step count or other activity level with the externally received step count or activity level.

In various exemplary embodiments a range of different information may be sensed and displayed to the user. For example, in at least one embodiment, control buttons 162, 164, 166 may be used to display heart rate, fluid consumption, and step count respectively, or similar controls may be accessed via a touchscreen display. In at least one embodiment, display controls may be programmed to display any available information to the user via display device 160.

In various exemplary embodiments, the valve mechanism is designed to preserve open volume below the top surface 114 of housing 104 in the area opposite opening 112 such that cavity 150 may be positioned in the best possible location to be viewed by the user without the need to increase the size or volume of the housing 104. In an exemplary embodiment of the invention, the valve actuator may include a generally U-shaped section that extends laterally to a point adjacent to or in contact with the valve seal 132 on the upper portion of the actuating side 134 in the resting position with the valve closed as described above to maintain space for cavity 150 in the best location within housing 104.

In various exemplary embodiments of the invention, the cap may include a measurement device and display that inform the user of how much fluid has been dispensed from the beverage container over a specified period of time, such as a day or any other suitable time frame. In at least one embodiment, the cap may include any type of flow meter, measurement, or estimation system to determine or estimate how much fluid has been dispensed, and a display, such as a display as described above, to inform the user of this information.

Figure 10:
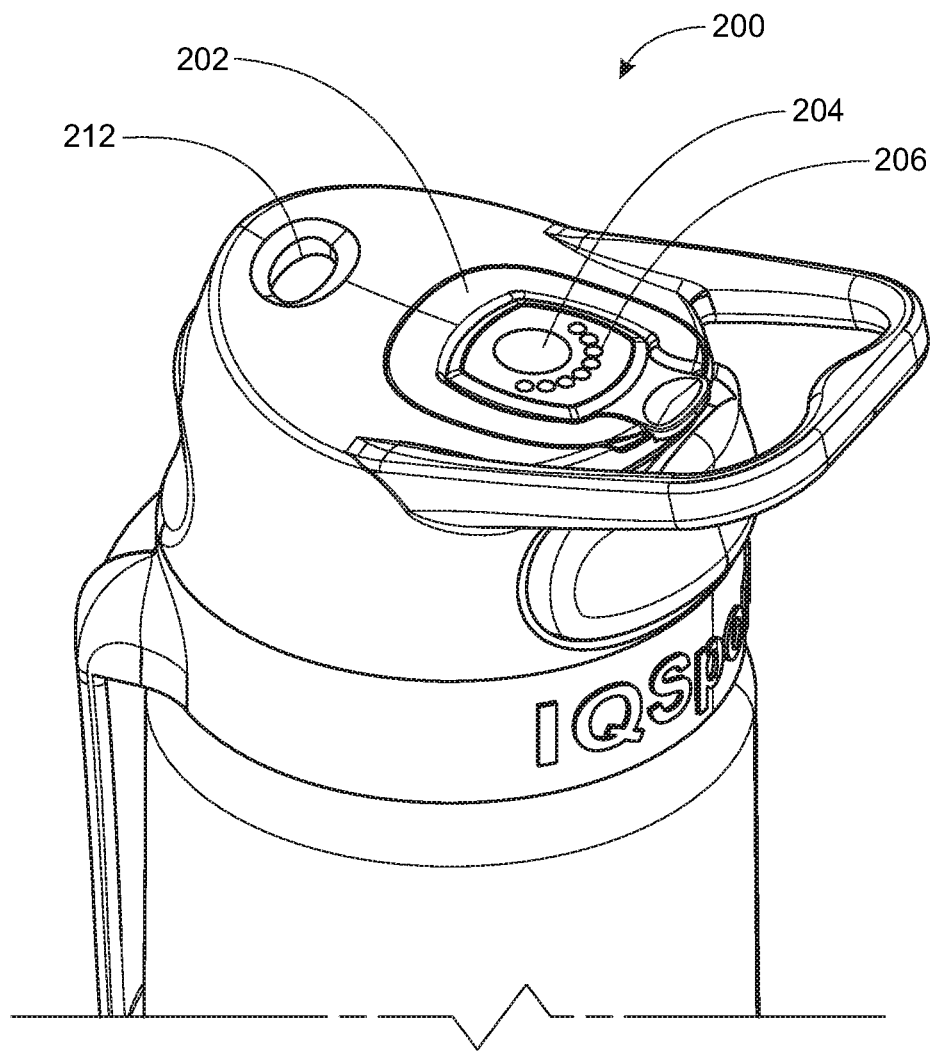
FIG. 10 is perspective view of an exemplary embodiment of a container cap in accordance with an embodiment of the invention.

FIG. 10 is perspective view of an exemplary embodiment of a container cap in accordance with an embodiment of the invention. As shown in FIG. 10, in various exemplary embodiments, a cap 200 may include a display housing 202 with a control button 204 and a plurality of small indicator lights 206. In at least one embodiment, the control button may be used to reset the display or program it to output different information. The indicator lights, in one or more embodiments, may be used to indicate the amount of fluid that has been dispensed since the last reset, or over a particular period of time such as a day or a week, by sequentially lighting up as additional fluid is dispensed. In at least one embodiment, such a system may automatically reset at a certain time interval, such as every day. As such, in at least one embodiment, this allows the user to quickly determine how much fluid they have consumed. In various exemplary embodiments, the indicator lights may be replaced with an LED display, an LCD display, bar graphs, numerical outputs, etc., or a combination thereof.

In various exemplary embodiments, the electronics housing may be detachable such that the cap may be cleaned separately in the dishwasher. As discussed above, in various exemplary embodiments, digital storage, processing, and communications may be provided to manage data collected by such systems. Communications such as one or more of Bluetooth, WiFi, WAN, NFC, cellular, etc., in one or more embodiment, allow the system to communicate with smartphones, laptops, networks, cloud-based systems, etc. to transfer, exchange, or receive information for storage or display to the user. Such systems, in at least one embodiment, allow the user to transfer information gathered during their activities for storage and use without the need to carry any additional electronic devices.

In various exemplary embodiments, the amount of fluid that has been dispensed from the beverage container may be determined or estimated using a variety of different techniques and devices. In one exemplary embodiment, an electronic switch may be placed in parallel with the water valve located in the cap such that when the valve is activated, the switch is opened or closed. In at least one embodiment, the switch may be connected to a timer that tracks the amount of time the water valve is kept open, which in turn may be used to calculate the amount of fluid dispensed based on the average flow rate through the opening 212. The switch may be coupled with the button utilized to open and close the valve for example.

By way of one or more embodiments, a more accurate estimate may be obtained by including a sensor that may determine when the beverage container is tilted. In at least one embodiment, the sensor may be oriented such that it activates when the beverage container is tilted into the drinking orientation, such that the timer may only be activated when the beverage container is in position to dispense the fluid. Further accuracy may be obtained by the use of a small probe to sense the presence of fluid near the opening 212, in at least one embodiment of the invention, such that the timer may only be activated when fluid is present near the opening. In one or more embodiments, an additional water sensor may be placed near the top of the beverage container to differentiate between sipping (lower water or fluid level) and pouring out at maximum flow (higher water or fluid level). In at least one embodiment, two separate timers and a conversion may be used to further increase the accuracy of the estimated consumption.

In various exemplary embodiments, a direct flow measurement device may be installed inline to precisely measure the actual flow of fluid out of the beverage container.

Figure 11:
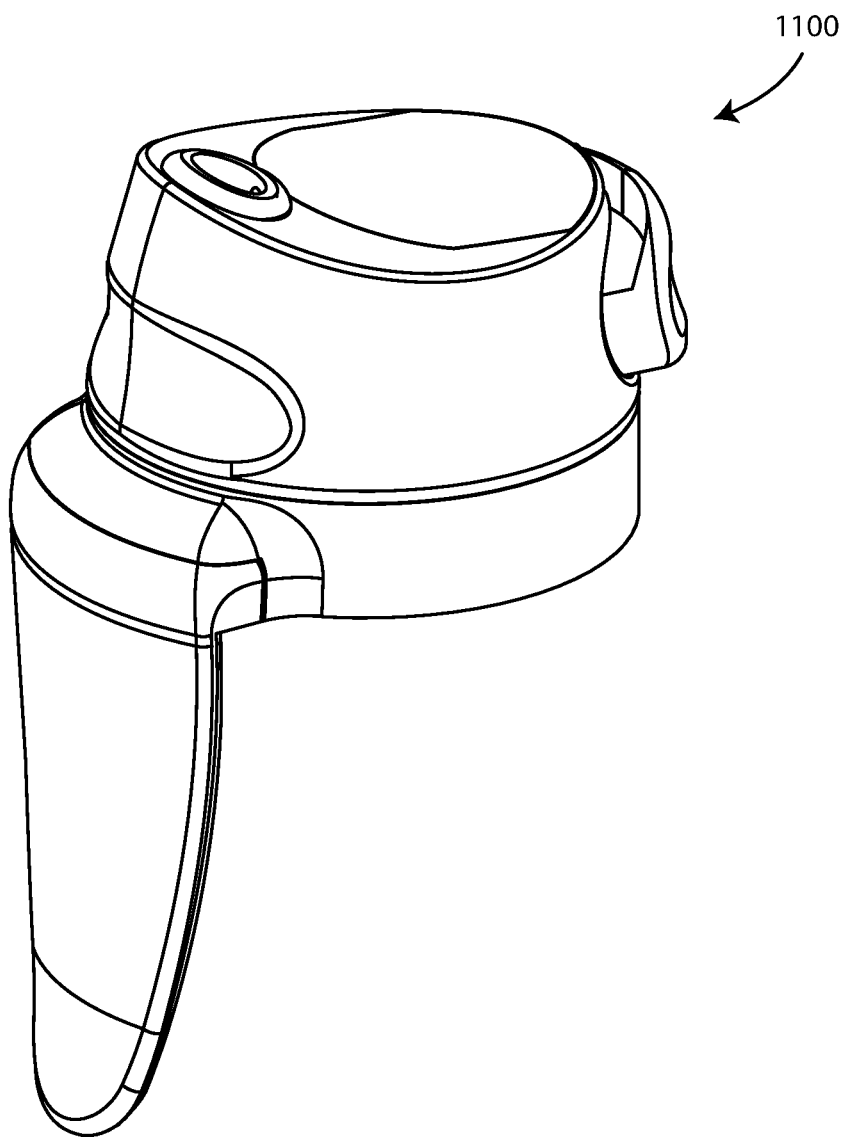
FIG. 11 is perspective view of an exemplary embodiment of the system.
Figure 12:
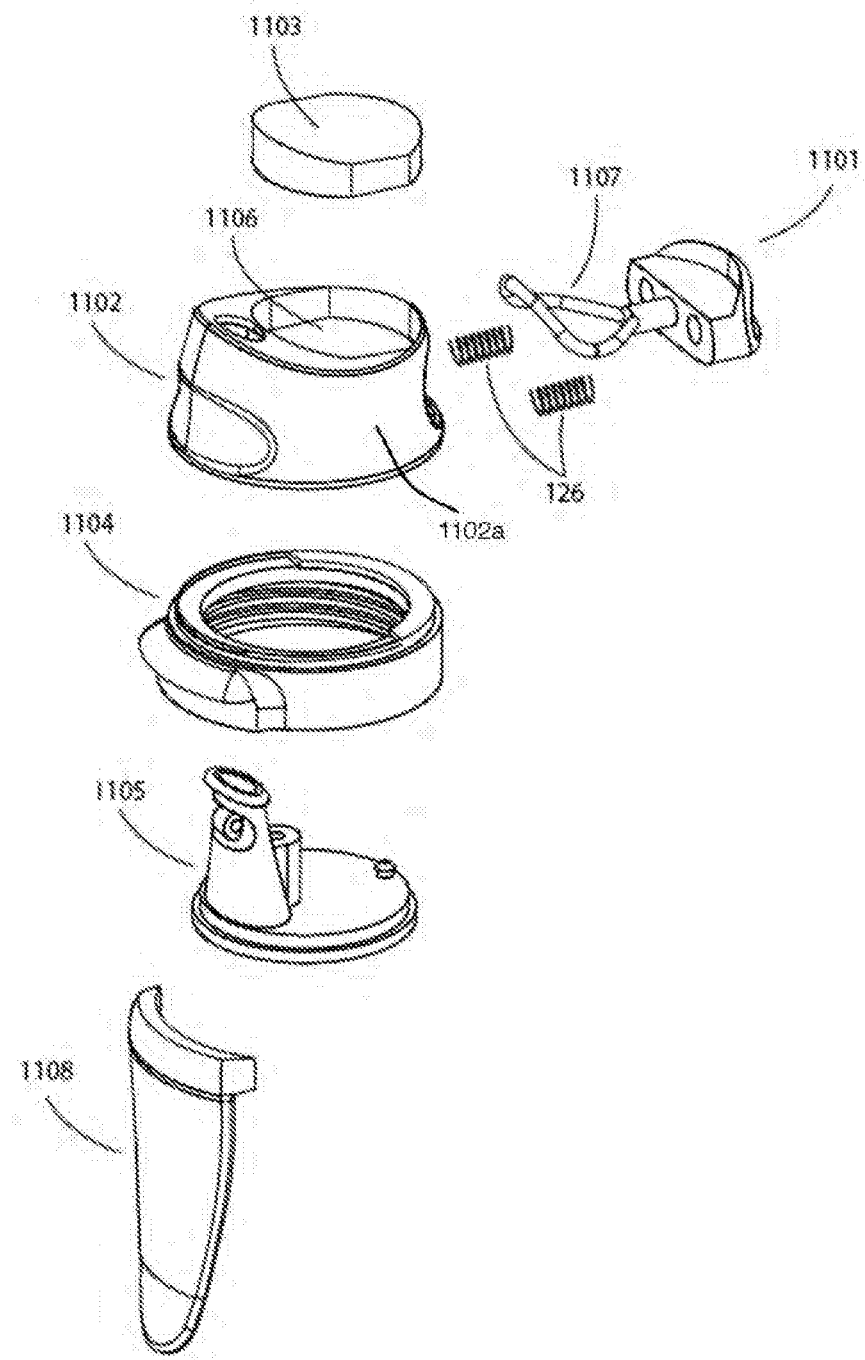
FIG. 12 is an exploded view of an exemplary embodiment the system.

FIG. 11 is perspective view of an exemplary embodiment of the system and FIG. 12 is an exploded view of an exemplary embodiment of the system.

Figure 13:
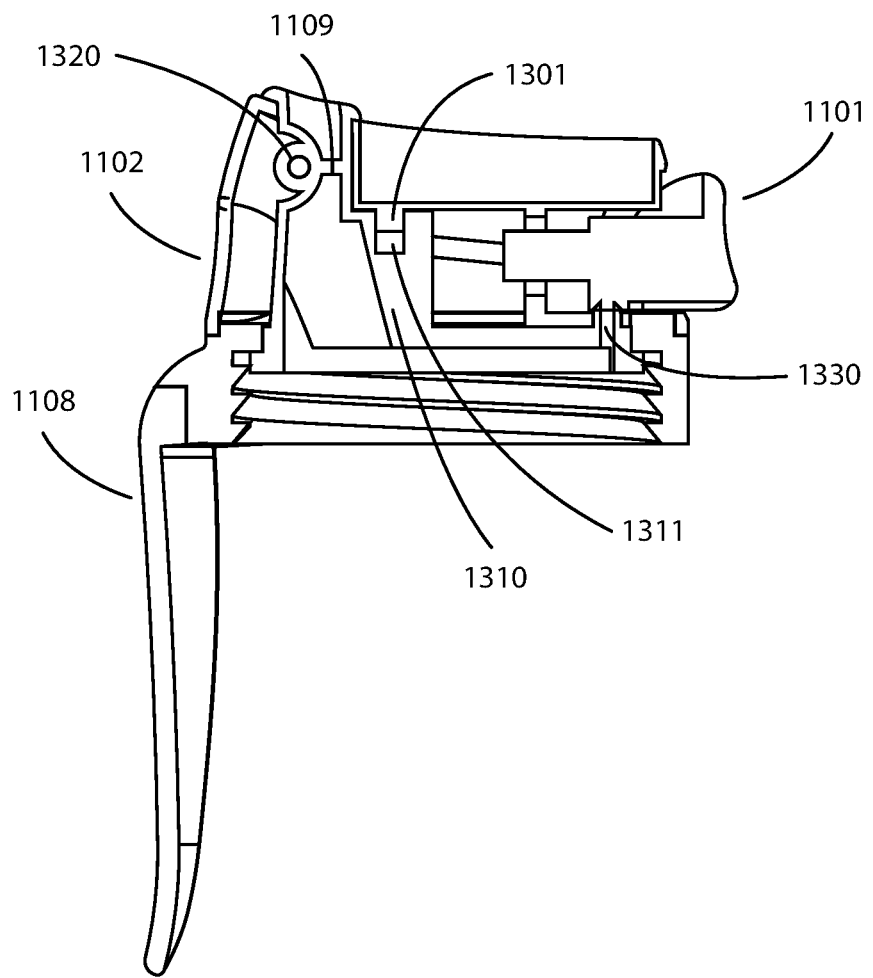
FIG. 13 is an internal side view of an exemplary embodiment of the system.

As shown in FIGS. 11 and 12, in at least one embodiment of the invention, the system 1100 for a beverage container may include one or more of a button 1101 with at least one arm 1107, a base element 1104 with a base element outer surface, and a flexible seal valve 1105 with a slit (as shown in FIG. 13 and described further below). In at least one embodiment, the system 1100 may be attached, in an adaptable manner, to a wide range of beverage containers of different shapes and sizes. By way of at least one embodiment, the base element 1104 may be coupled with a beverage container and moveably coupled with the button 1101. Optional springs 126 may fit into holes in the button to put the button back out, or if the valve is resistant enough, then the springs may not be required as the valve in one or more embodiments may return to the closed position without external force.

By way of one or more embodiments, the button 1101 may include two parts such as a first structure including a pressable cap and a second structure including the at least one arm 1107. In at least one embodiment, the first structure may be structured orthogonally to at least a portion of the at least one arm 1107, such that at least a portion of the button 1101 includes a substantially T-shaped structure. In one or more embodiments, the first structure and the second structure of the button 1101 may include a dishwasher-safe plastic material. In at least one embodiment of the invention, the flexible seal valve 1105 may include a dishwasher-safe flexible material such as rubber, silicone, or any other type of elastomer.

At least one embodiment of the invention may include a top element 1102 coupled with the base element 1104 and the flexible seal valve 1105, wherein the top element 1102 may include at least one hole. One or more embodiments of the invention may include one or more of a clip element 1108, and a handle (not shown) coupled with the top element 1102. By way of one or more embodiments, the clip element 1108 may attach to the base element 1104 on the base element outer surface.

According to one or more embodiments, the top element 1102 includes a top element outer surface 1102a and may include at least one compartment 1106 formed on the top element outer surface. At least one embodiment of the invention includes a timer, such as timer 2115 shown in FIG. 21, and at least one electronic element 1103 that may be situated in the at least one compartment 1106, and at least one sensor, such as at least one sensor 2116 shown in FIG. 21, that senses one or more signals and data packets. In one or more embodiments, the at least one electronic element 1103 may be situated in a single compartment 1106, or one or more electronic elements of the at least one electronic element 1103 may be situated in various compartments 1106. In at least one embodiment, the at least one electronic element 1103 may include an independent housing, wherein the at least one electronic element 1103 is situated within the independent housing, and the independent housing is situated within the at least one compartment 1106. According to one or more embodiments, the at least one electronic element 1103 and/or the housing of the at least one electronic element may include at least three plastic parts including a top structure, a bottom structure and middle structure. In at least one embodiment, the at least one electronic element 1103 and/or the housing of the at least one electronic element may include a power source such as a battery, and a power source or battery door situated on an outer surface of the at least one electronic element 1103 and/or the housing of the at least one electronic element. In one or more embodiments, the power source may be a rechargeable power source or may be a self-charging and re-charging power source.

Figure 21:
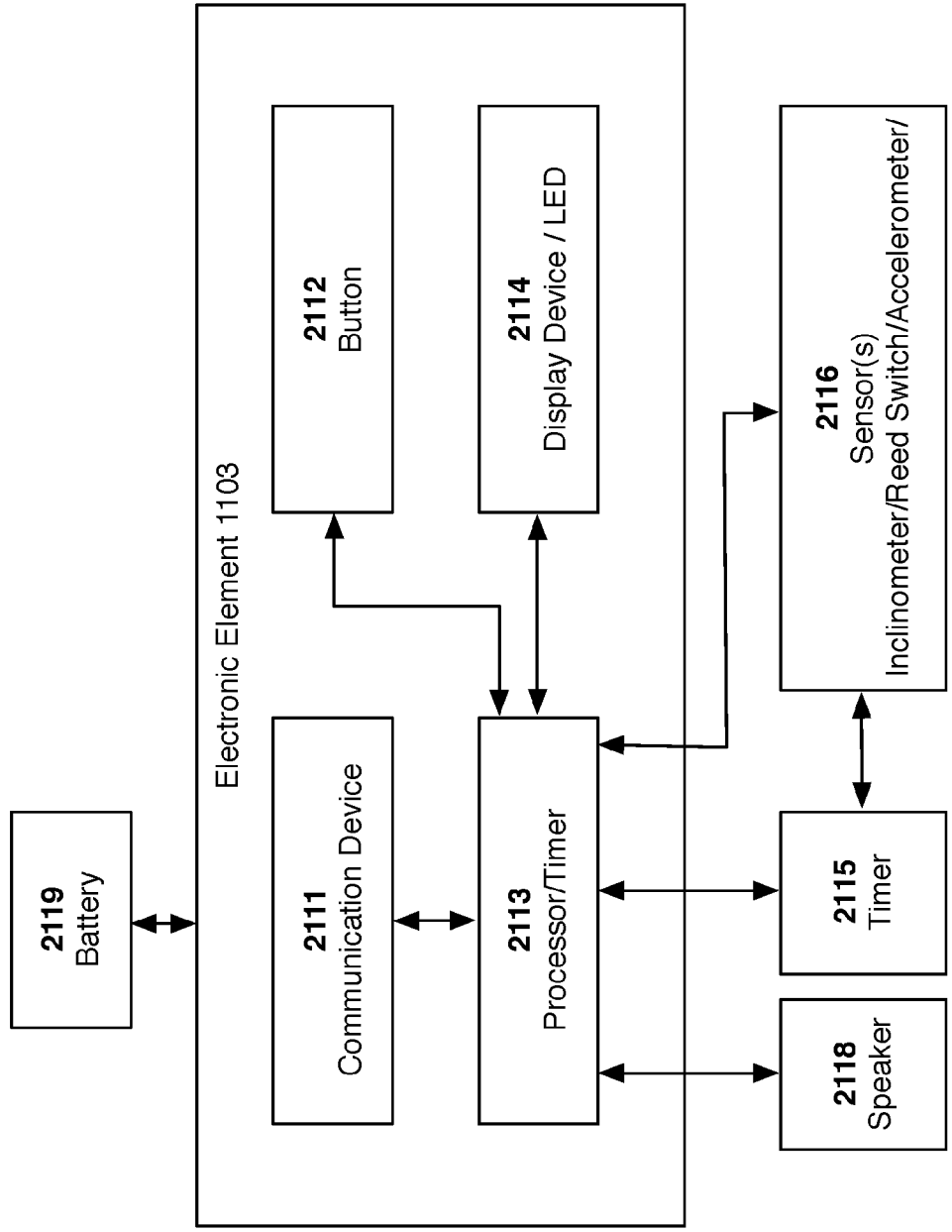
FIG. 21 is a structural view of an exemplary embodiment of the invention.

In at least one embodiment, the at least one electronic element 1103 may include the timer (internal to processor or tightly coupled to processor 2113, or external 2115) and the at least one sensor 2116. In one or more embodiments, the at least one electronic element 1103 may include one or more of a processor, such as processor 2113 shown in FIG. 21, one or more function buttons 2112, and at least one display device and/or LED 2114, as shown in FIG. 21. Embodiments may also include battery 2119 and speaker or other acoustic input/output device 2118. Embodiments may communicate with other devices via communications device 2111 and obtain button press events from button interface 2112, which may couple with a mechanical switch and/or button for example. According to at least one embodiment, the at least one display device may include at least one screen such as a touch-screen, a light emitting device, and a tactile device such as a vibration element and a braille element. In at least one embodiment, one or more of the timer, the one or more function buttons, the at least one electronic element 1103 and the at least one sensor may be directly or indirectly connected to one another. In at least one embodiment, the at least one sensor, such as the at least one sensor 2116 shown in FIG. 21, may include at least one inclinometer 2116 or any other type of orientation sensor capable of detecting an angle of orientation of the cap and thus container, or any other component capable of determining the orientation of the system, at least one activity level sensor 2116, at least one thermometer 2116 or at least one weight sensor 2116, or a combination thereof, for example in an integrated sensor package 2116. Alternatively, weight sensors may couple between handle 106 and 104, for example where handle 106 pivots. In one or more embodiments, the inclinometer may be utilized as the activity level sensor.

Specifically, in one or more embodiments, the inclinometer may be utilized by the system as the activity level sensor by sampling the orientation angle over time and determining when the angle has changed over a predefined threshold from the last orientation angle value previously sampled. In addition, embodiments may also utilize the inclinometer and timer to determine when the cap has tilted over an angle that allows fluid to flow through the device, and for how long to determine the amount of fluid dispensed. In this manner the inclinometer may be utilized in a very cost effective manner as an activity level sensor and flow meter as will be described further below.

One or more embodiments of the invention may include a user interface located on or near or part of one or more of the top element 1102, the at least one compartment 1106, the at least electronic element 1103, the base element 1104, and the clip element 1108. The user interface, in at least one embodiment, may include the one or more function buttons, may be a touchscreen or may include other user input devices coupled with, communicatively or directly, to the at least one sensor, the timer and the at least one electronic element 1103.

By way of one or more embodiments, the at least one sensor may include at least one inclinometer that detects at least one tilt angle of the beverage container when the beverage container is tilted, such as in a drinking orientation. In at least one embodiment, when the beverage container is tilted at the at least one tilt angle, the inclinometer and the processor may determine an average tilt angle over a period of time the beverage container is tilted, may determine if the flexible seal valve 1105 is open, and may activate the timer to measure an amount of time the beverage container is tilted. In one or more embodiments, when the beverage container is tilted, the processor may determine a volume of fluid dispensed from the beverage container based on the at least one tilt angle and the amount of time the beverage container is tilted as determined by the timer.

According to at least one embodiment, the at least one inclinometer may be oriented such that the at least one inclinometer is activated to determine the at least one tilt angle when the beverage container is tilted into the drinking orientation such that the timer would only be activated when the beverage container is in position to dispense the fluid. To increase accuracy of detecting a tilt angle and ensuring the beverage container is in a drinking orientation, at least one embodiment of the invention may include a small probe to sense the presence of fluid near an opening, such as opening 212 of FIG. 10, or near the slit 1109 in the flexible seal valve 1105 (as will be discussed below), such that the timer would only be activated when fluid is detected by the probe. In one or more embodiments, an additional fluid sensor may be placed near, on, or within the top element 1102 to differentiate between sipping (lower fluid or water level) and pouring out at maximum flow (higher fluid or water level).

By way of one or more embodiments, the probe may include a capacitance probe, a resistance probe, an ultrasonic sensor, an optical sensor, a mechanical float, a pressure sensor, or any other suitable probe or a combination thereof. In at least one embodiment, the probe may extend from the top element 1102, or the base element 1104, to the flexible seal valve 1105. In one or more embodiments, the probe may be built-in or integrated with or attached directly to the flexible seal valve 1105, and may feed data or relay detected signals to the at least one electronic element 1103, to the timer, to an external device, and/or to the at least one display device. In at least one embodiment, two or more separate timers and at least one conversion may be used to further increase the accuracy of the estimated consumption or estimated dispensing of the fluid.

In at least one embodiment of the invention, the processor may indicate on the at least one display device one or more of the volume of fluid dispensed from the beverage container, the average tilt angle, the fluid level, the fluid dispensing flow rate, instructions regarding the amount of fluid left to dispense, and the amount of time the beverage container is tilted or amount of time the fluid has dispensed from the beverage container. One or more embodiments may compute the volume dispensed when a tilt angle is over a particular predefined angle by multiplying the known flow rate through the particular size opening, Flow rate=Volume/time by the time t to produce the volume: V=F*t. For example if the hole in the top element or slit, or whichever is smaller, allows a Flow rate F of one liter per minute, and if the apparatus is tipped over a predefined angle of for example 10 degrees as detected by the integrated inclinometer, then a timer starts while the apparatus at least at that orientation or higher and the timer stops when the inclinometer determines that the apparatus is tilted down below the predefined angle, e.g., for 3 seconds. At that time, the apparatus may calculate the volume dispensed as V=(1 liter/60 seconds)*3 seconds=0.05 liters.

According to one or more embodiments of the invention, the at least one sensor may include an activity level input sensor that obtains at least one activity level input or a sensor that measures the at least one activity level of a user of the beverage container to determine an amount of fluid a user of the beverage container should consume.

In one or more embodiments, the processor may calculate the amount of fluid a user of the beverage container should consume depending on one or more of the intensity of the activity and movement levels, the duration of the activity and movement, and on a comparison to previously saved history logs of the user's fluid consumption habits and/or previously stored sensor signals. In at least one embodiment, the at least one sensor may indicate the amount of fluid on the at least one display device, such as via the processor. In one or more embodiments, the processor and the at least one activity level sensor may display the average activity level, the volume of fluid dispensed from the beverage container, the fluid dispensing flow rate, instructions regarding the amount of fluid left to dispense, and the changes in the amount of fluid the user should consume based on the input or detected activity level. In one or more embodiments the user may assert a button on the electronics package to indicate that the container has been refilled, wherein the processor may recalculate any remaining amount to be consumed for a given time frame.

In one or more embodiments, the at least one activity level sensor may detect a user's step count to determine the amount of fluid the user should consumer, wherein the user's step count and the amount of fluid determined may be displayed to the user on the at least one display device. In at least one embodiment, the user's step count may be measured using an electronic accelerometer of any type, mechanically such as using a weighted spring that contacts a switch, flexes a piezomembrane, or flexes a strain gauge, a vibration sensor, or by any other suitable measuring device that may be located within the top element 1102, or within the at least one compartment 1106, or as part of the at least one electronic element 1103.

Embodiments may obtain activity from external sensors wirelessly for example. In one or more embodiments, a mobile phone with GPS may send distance traveled to the system, which then used the distanced traveled or elevation change, for example along with temperature to determine activity.

Figure 22:
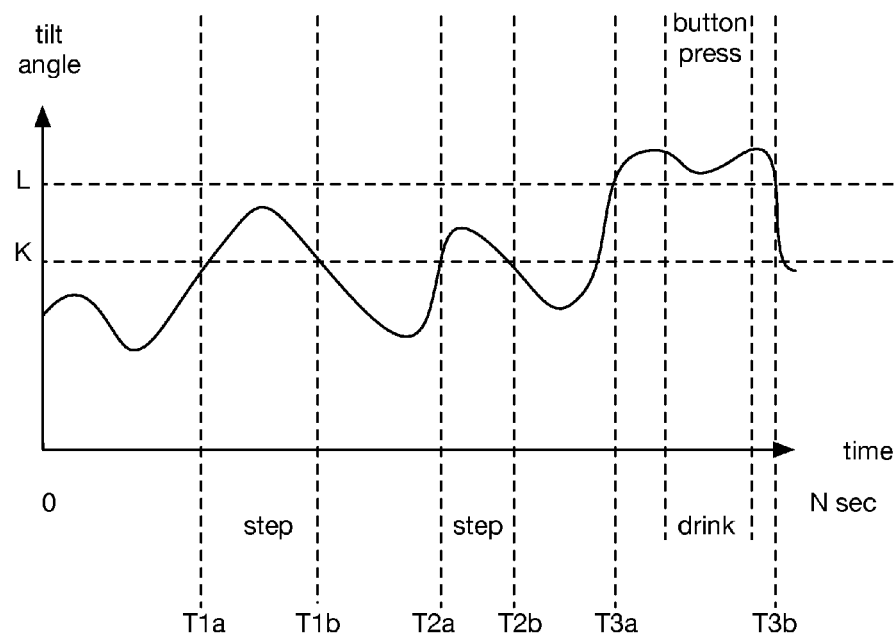
FIG. 22 illustrates a graphical view of the calculation of activity level using an inclinometer as an activity level sensor and as a liquid flow meter.

In other low cost or standalone embodiments, the inclinometer may be sampled over time to determine if the angle of orientation is changing over a predefined threshold over time. If so, a "step" may be added to the total number of steps that the user has taken for example. When a predetermined level of activity has occurred, the user may be prompted to drink a particular volume of liquid from the container. In this manner, the inclinometer, which is relatively inexpensive, may be utilized to provide both activity level sensor and flow meter capabilities with only one component. This allows use of a lower power component, for example a 1-axis sensor, compared to N-axis devices that are more expensive in cost and power. FIG. 22 illustrates a graphical view of the calculation of activity level using an inclinometer as an activity level sensor and as a liquid flow meter. As shown, the processor obtains the inclinometer angles over time and when a previous tilt angle is below a particular threshold angle K, and a current reading exceeds the threshold angle K, then a "step" count may be incremented in the memory of the processor. Embodiments may utilize a derivative of the slope of the inclinometer or any other processing of the samples, which may occur at discrete times at any portion of time between 0 and N seconds for example. Exemplary steps are shown between times T1$a$ and T1$b$, and T2$a$ and T2$b$. The processor may query the timer 2115 for a time duration when a first step is encountered for example, wherein the total number of steps divided by the duration of activity time N as shown, yield the activity level. The processor may utilize any type of false positive processing including determining if the number of tilts per second is below or above a threshold indicative of steps for example. This enables embodiments to differentiate steps from a scenario such as the bouncing of a beverage container within a vehicle for example. In this manner a simple yet effective step count or activity level may be calculated using the same sensor used to determine the amount of liquid consumed. If the tilt angle exceeds angle L for a predetermined time, then a drink event may be stored in memory. As shown, between times T3$a$ and T3$b$, and optionally in combination with any other sensors that directly or indirectly determine that liquid is present in or near the hole of the cap, the volume of liquid is calculated as the volume per second possible through the hole multiplied by (T3$b$–T3$a$) seconds. One or more embodiments may utilize the button to determine when the valve is open, for example by detecting the button assertion, for example with the processor coupled with a switch that is asserted by the button, or wherein the button itself may be sampled to obtain its open/closed state, to determine when to track the time of the button press when the valve is actually open to calculate the amount of liquid dispensed, alone or in combination with other sensors that actually detect flow of liquid through the valve for example.

In one or more embodiments, the at least one sensor may include at least one thermometer that measures an external temperature external to the beverage container. In at least one embodiment, the at least one display device may indicate an amount of fluid a user of the beverage container should consume based on the external temperature, such as via the processor using an algorithm to calculate the amount of fluid the user should consume based on the detected external temperature, the difference in temperature and the difference in fluid the user should consume based on the difference in temperature. By way of one or more embodiments, the at least one display device may display on a screen, via a light-emitting element or via a tactile element the external temperature as a number, as a range via different colored light-emitting elements, or as a heated or cooled tactile element that is heated or cooled to the detected external temperature. In at least one embodiment, the at least one thermometer and the processor may activate the at least one display device at a first temperature to display the first temperature and indicate an amount of fluid the user should consume at the first temperature at a first time period. In one or more embodiments, the at least one thermometer and the processor may activate the at least one display device at one or more second temperatures to display the one or more second temperatures and indicate an amount of fluid the user should consume at the one or more second temperatures at one or more second time periods after the first time period. Any deviation from the predefined amount of liquid to be consumed by a user, for example as determined by the medical community is in keeping with the spirit of the invention. For example, this may include increasing the amount of liquid by 3 percent as required for every 5 degrees increase in ambient air temperature or for every 7 percent of increase in humidity, or using any other formula, function, table or external input to deviate from the predefined volume for the user. Any other values including sunshine as determined by a photometer integrated into any portion of the apparatus to determine whether sunny or cloud may also be utilized. Age, weight, medical condition or any other value may also be utilized to deviate from the predefined amount of liquid to consume in keeping with the spirit of the invention.

In at least one embodiment of the invention, the at least one communication device accepts information from the external device and passes the information to the processor and wherein the processor is configured to determine, or, wherein the external device is configured to determine an amount of fluid a user of the beverage container should consume based on an age of the user, weight of the user, temperature, humidity, sunny or cloudy value, activity level, time of day or time since last drink, activity level, motion, altitude, medical needs, number of steps, heart rate, respiration rate, blood pressure, blood oxygen level, hydration value obtain from the user, or any combination thereof. In one or more embodiments, the at least one communication device accepts information from the processor and passes the information to the external device to display the information and wherein the information includes at least information related to an amount of fluid.

In at least one embodiment of the invention, the at least one sensor may include at least one weight sensor. In one or more embodiments, the at least one weight sensor may be coupled between the clip element 1108 and the base element 1104, or coupled between the handle and the top element 1102. This enables a standalone method of determining the amount of liquid remaining, for example by utilizing any time averaging or other formula or sensor to account for motion. Alternatively, or in combination, the timer and inclinometer may be utilized to calculate the amount dispensed and correlate the weight to more accurately gauge the amount of volume remaining and therefore dispensed already.

In one or more embodiments, the processor and the at least one display device may accept a weight of a user of the beverage container, for example via the one or more function buttons or the at least one display device, or communicatively via and external device, to determine an amount of fluid a user of the beverage container should consume based on the accepted input weight, and may indicate the amount of fluid that should be consumed by the user on the at least one display device. In at least one embodiment, the at least one display device may indicate an amount of fluid a user of the beverage container should consume based on the detect weighted via the processor, such as using an algorithm that may calculate the necessary fluid amount based on the detected weight, the difference in weight and the difference in fluid the user should consume based on the difference in weight. For example, in at least one embodiment, the algorithm may include an equation of Weight in lbs./2 to equal the minimum number of ounces of fluid the user should consume per day as for example determined by the medical community. Any other predefined starting amount may be utilized in keeping with the spirit of the invention.

According to at least one embodiment, the at least one sensor may be placed at various appropriate locations throughout the system 1100 including near or on the button 1101, near or on the top element 1102, near or on the at least one compartment 1106, near or on or part of the at least electronic element 1103, near or on the base element 1104, near or on the flexible seal valve 1105, and/or near or on the clip element 1108. In one or more embodiments, the at least one sensor, the processor, the timer and the at least one display device may measure, store, calculate, accept, determine and display data and signals instantly or over a course of time. In at least one embodiment, the data that is one or more of measured, stored, calculated, accepted, determined and displayed may include one or more of the user's heart rate, respiration rate, blood pressure, blood oxygen level, hydration or any other physiological characteristics. In at least one embodiment, the data may include a location of the user, and activity information such as physical location, temperature, humidity, barometric pressure, time, elapsed time, number of steps, alarms, altitude, health critical conditions such as pregnancy, nursing, diabetes, obesity, or any other medical circumstance requiring an above normal consumption of fluids or water.

By way of at least one embodiment of the invention, the at least one electronic element 1103 may include at least one communication device that communicates with at least one external device to relay the one or more signals sensed by the at least one sensor and/or the outputs of the timer, and/or the indications of the at least one display device. In one or more embodiments, the at least one communication device may accept information from the external device to determine an amount of fluid a user of the beverage container should consume based on an age of the user, weight of the user, temperature, any other sensed signal data, or any combination thereof. By way of at least one embodiment, the at least one external device may include a mobile device such as a mobile device, mobile smartphone, a stationary device, a computer, or any other computer processing device.

In one or more embodiments, the at least one communication device may be used for digital storage, processing, and communications to one or more of manage, relay, allocate, accept, display and store data and signals determined, measured and calculated by the at least one sensor, the at least one electronic element 1103 and the timer. In at least one embodiment, the at least one communication device may communicate using one or more communication techniques such as Bluetooth, WiFi, WAN, NFC, cellular, LPWA (Low-power Wide Area sometimes referred to as M2M), etc., in order to communicate with one or more of smartphones, laptops, networks, cloud-based systems, and any other external device as discussed above. According to at least one embodiment, the at least one signal, data and information detected, determined, measured and calculated may be communicated to the at least one external device, such as a remote device, for one or more of storage, compilation, analysis and display.

According to one or more embodiments of the invention, the at least one electronic device 1103 may include a start button that may be activated or pressed in the morning, or at a starting point of a user's day. In at least one embodiment, the start button may be manually pressed or activated and/or may be automatically activated, such as via a pre-set user setting for a specific time of day to allow the processor to automatically activate the start button or may be manually activated or pressed instantly by the user. In one or more embodiments, the pre-set user setting or automatic activation may be based on a time of day, a pre-set time of day set into the at least one electronic element 1103, the number of hours the user has been awake and active, a pre-set sleep mode or setting and based on an alarm clock setting. For example, in one or more embodiments, the at least one electronic element 1103 may communicate with an external alarm clock, wherein the at least one electronic element 1103 may accept a wake-up signal to activate the start button and the timer from the external alarm clock.

In one or more embodiments, the at least one display device may include at least one light-emitting diode (LED) coupled with the timer and with the at least one sensor. In at least one embodiment, the at least one LED may flash to indicate, for example to a user, one or more time periods to consume the fluid as determined by the timer and whether enough fluid has been consumed by the user as determined by the at least one sensor. In one or more embodiments, the at least one LED may remain flashing until enough fluid has been consumed by the user at the one or more time periods, as determined by the timer and the at least one sensor. In at least one embodiment, the start button may be manually or automatically pressed or activated to manually or automatically restart the timer to determine the one or more time periods.

By way of one or more embodiment, the at least one LED may flash to indicate the time to consume a first amount of the fluid at a first time period of the one or more time periods and may remain flashing until the first amount of the fluid has been consumed by the user. In at least one embodiment, after a pre-determined and/or pre-set amount of time after the first amount of fluid has been consumed, the at least one LED may flash to indicate the time to consume a second amount of the fluid at a second time period after the first time period, and may remain flashing until the second amount of the fluid has been consumed by the user. In one or more embodiments, the pre-determined and/or pre-set amount of time may be pre-set and/or pre-determined by a user, or pre-calculated and pre-set by the processor based on previously sensed signals and information from one or more of the timer, the at least one electronic element 1103 and the at least one sensor.

In at least one embodiment, the at least one LED may include different respective LED lights for each time period or amount of fluid in the beverage container, such as one or more of different colors, different sizes, different flash repetition rates, and different shapes. As such, in one or more embodiments, each LED light may flash in a specific manner respectively according to one or more of a specific time period, the amount of fluid left in the beverage container, and the amount of fluid the user should consume.

According to at least one embodiment, the at least one electronic element 1103 may include at least one sound emitting device coupled with the timer and the at least one sensor. In one or more embodiments, the at least one sound emitting device may beep to indicate one or more time periods to consume the fluid as determined by the timer and whether enough fluid has been consumed by the user as determined by the at least one sensor. In at least one embodiment, the at least one sound emitting device may remain beeping until enough fluid has been consumed by the user at the one or more time periods, as determined by the timer and the at least one sensor. In at least one embodiment, the start button may be manually or automatically pressed or activated to manually or automatically restart the timer to determine the one or more time periods.

By way of one or more embodiment, the at least one sound emitting device may beep to indicate the time to consume a first amount of the fluid at a first time period of the one or more time periods, and may remain beeping until the first amount of the fluid has been consumed by the user. In at least one embodiment, after a pre-determined and/or pre-set amount of time after the first amount of fluid has been consumed, the at least one sound emitting device may beep to indicate the time to consume a second amount of the fluid at a second time period after the first time period and may remain beeping until the second amount of the fluid has been consumed by the user. In one or more embodiments, the pre-determined and/or pre-set amount of time may be pre-set and/or pre-determined by a user, or pre-calculated and pre-set by the processor based on previously sensed signals and information from one or more of the timer, the at least one electronic device and the at least sensor.

In at least one embodiment, the at least one sound emitting device may include one or more of respective different sounds with one or more of different frequencies, beats, repetitions and volumes for each time period or amount of fluid in the beverage container. As such, in one or more embodiments, each sound-emitting device may beep in a specific manner respectively according to one or more of a specific time period, to the amount of fluid left in the beverage container, and to the amount of fluid the user should consume.

By way of at least one embodiment, one or more of the at least one display device and the at least one sound-emitting device may each include eight devices, such as eight LEDs, for each 64 ounces of fluid or water, such that each LED is activated for 8 ounces of fluid or water. As such, in at least one embodiment, each of the eight display devices and/or the sound-emitting devices may flash, and/or beep, or generate any other type of output, until the respective 8 ounces of fluid have been consumed by the user.

At least one embodiment of the invention may include both the at least one display device, such as the at least one LED, and the at least one sound emitting device. In one or more embodiments, the at least one display device may flash independently of the beeping of the at least one sound emitting device, jointly with the beeping of the at least one sound emitting device or simultaneously with the beeping of the at least one sound emitting device. In at least one embodiment, the at least one display device may flash in an alternating manner with the beeping of the at least one sound emitting device, such that the at least one display device may flash first then the at least one sound emitting device beeps, or vice versa, continuously until the amount of fluid has been consumed by the user during the one or more time periods. By way of at least one embodiment, the at least one display device may include at least one screen and may display one or more of numerical outputs, shapes, graphs, symbols, colors, letters and words on the at least one display device or screen.

In one or more embodiments, the start button, or the one or more function buttons, may reset one or more of the at least one display device, the at least one sound-emitting device, the timer and the processor calculations. In at least one embodiment, the start button, or the one or more function buttons, may program one or more of the at least one display device and the at least one sound-emitting device to output different information and signals.

By way of at least one embodiment, one or more of the at least one display device and the at least one sound-emitting device may indicate the amount of fluid that has been dispensed since the last reset, or over a particular period of time such as a day or a week, by sequentially lighting up, or beeping, or vibrating or displaying information and signals as additional fluid is dispensed. In one or more embodiments, one or more of the at least one display device, the at least one sound-emitting device, the timer and the processor calculations may automatically reset at a certain time interval, such as every day, every week, every 2 weeks, etc., or a time interval as set by the user. As such, in at least one embodiment, the user is easily and reliable able to determine how much fluid has been consumed, and how much more fluid the user should consume.

FIG. 13 is an internal side view of an exemplary embodiment of an embodiment of the system. As shown in FIG. 13, in one or more embodiments, the flexible seal valve 1105 is coupled with the base element 1104, and the at least one arm 1107 is coupled with the flexible seal valve 1105. By way of at least one embodiment, the at least one arm 1107 may be coupled with the flexible seal valve 1105 to operatively open and close the slit 1109 in the flexible seal valve 1105 when the button 1101 is moved inwardly and outwardly respectively. In at least one embodiment, the at least one arm 1107 may be attached on an opposing side of the flexible seal valve 1105 in order to pull open and closed the slit 1109 to open and close the flexible seal valve 1105.

In one or more embodiments, the top element 1103 may cover the button 1101 and at least a portion of the flexible seal valve 1105. In at least one embodiment, the button 1101 may slide in and out of one or more of the top element 1102 and the base element 1104.

By way of one or more embodiments, the base element 1104 may include a first partially enclosed inner portion and the top element 1102 may include a second partially enclosed inner portion. As such, in at least one embodiment, the flexible seal valve 1105 may extend through and couple with the base element 1104 via the first partially enclosed inner portion and extend through and couple with the top element 1102 via the second partially enclosed inner portion.

In at least one embodiment, the button 1101 may be spring loaded, or include at least one spring, such as spring-loaded to the right, in order to pull the slit 1109 closed to form a seal in the flexible seal valve 1105. In one or more embodiments, the flexible seal valve may include at least one vent hole 1330, and may include a sliding seal between button 1101 and the at least one vent hole 1330 in the flexible seal valve 1105. In at least one embodiment, the elements of the system 1100 are protected and sealed from the fluid, except an inner portion of the flexible seal valve 1105 and an outer portion of the button 1101.

According to at least one embodiment of the invention, the flexible seal valve 1105 may include a top depression 1301 to secure a rear portion of the flexible seal valve 1105 within the top element 1102 and/or the base element 1104, a valve support 1310, a valve support indent 1311, a valve couple element 1320 and at least one vent hole 1330. In one or more embodiments, the valve support indent 1311 may remain stationary when the button 1101 is pressed.

Figure 14:
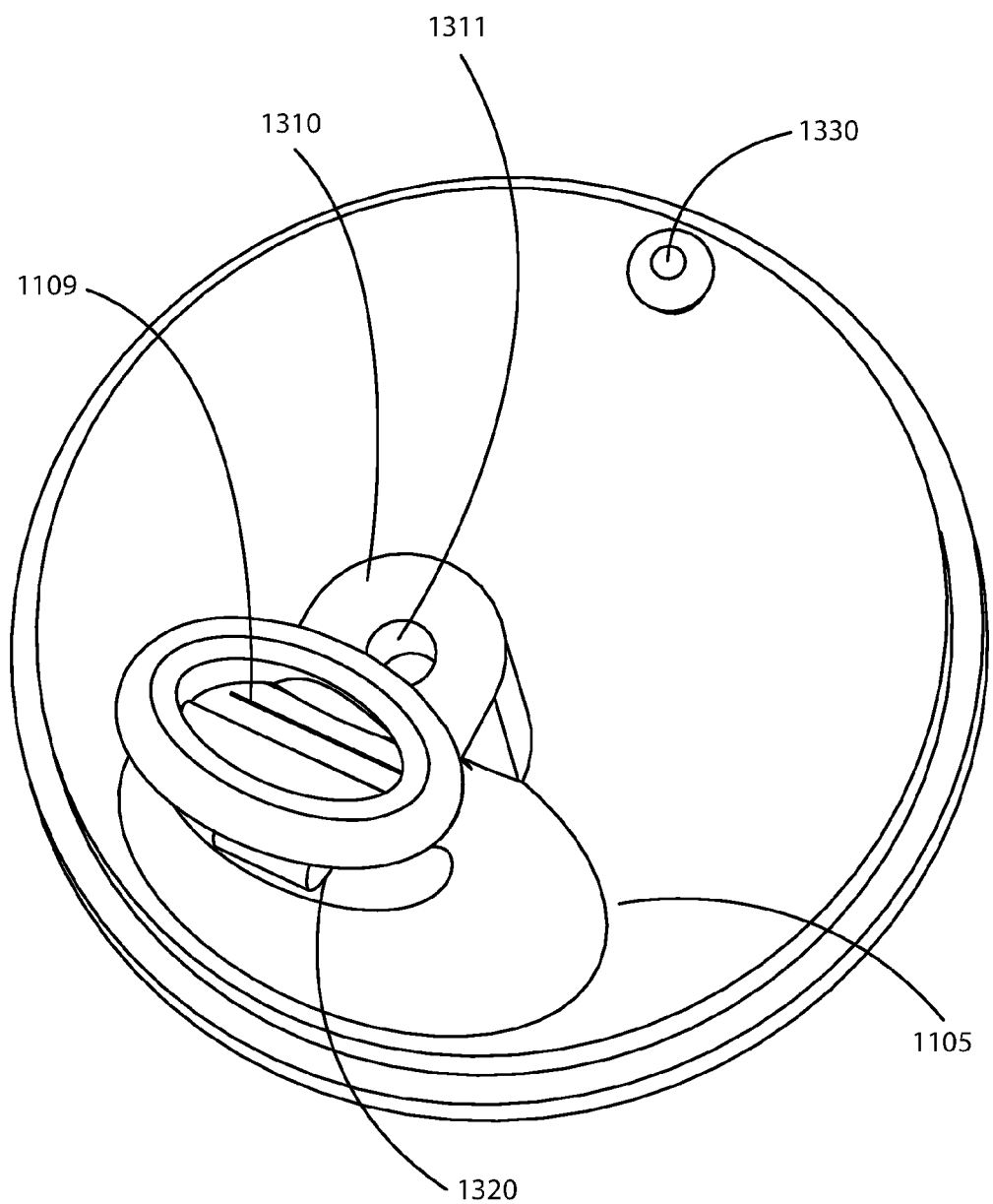
FIG. 14 is a top side view of an exemplary embodiment of a flexible seal valve.

FIG. 14 is a front side view of an exemplary embodiment of a flexible seal valve, according to at least one embodiment of the invention, depicting a top side view of the flexible seal valve 1105 with the slit 1109, the at least one vent hole 1330, the valve support 1310, the valve support indent 1311 and the valve coupling element 1320. In one or more embodiments, the flexible seal valve 1105 may include a circular base element, wherein the slit 1109, the at least one vent hole 1330, the valve support 1310, the valve support indent 1311 and the valve coupling element 1320 are located on the circular base element. In at least one embodiment, the circular base element may include an outer circumference edge, wherein the outer circumference edge includes two different heights, such that the outer circumference edge forms a step or threaded edge in order to securely couple, for example in a threaded manner, with an inner portion of one or more of the top element 1102 and the base element 1104.

Figure 15:
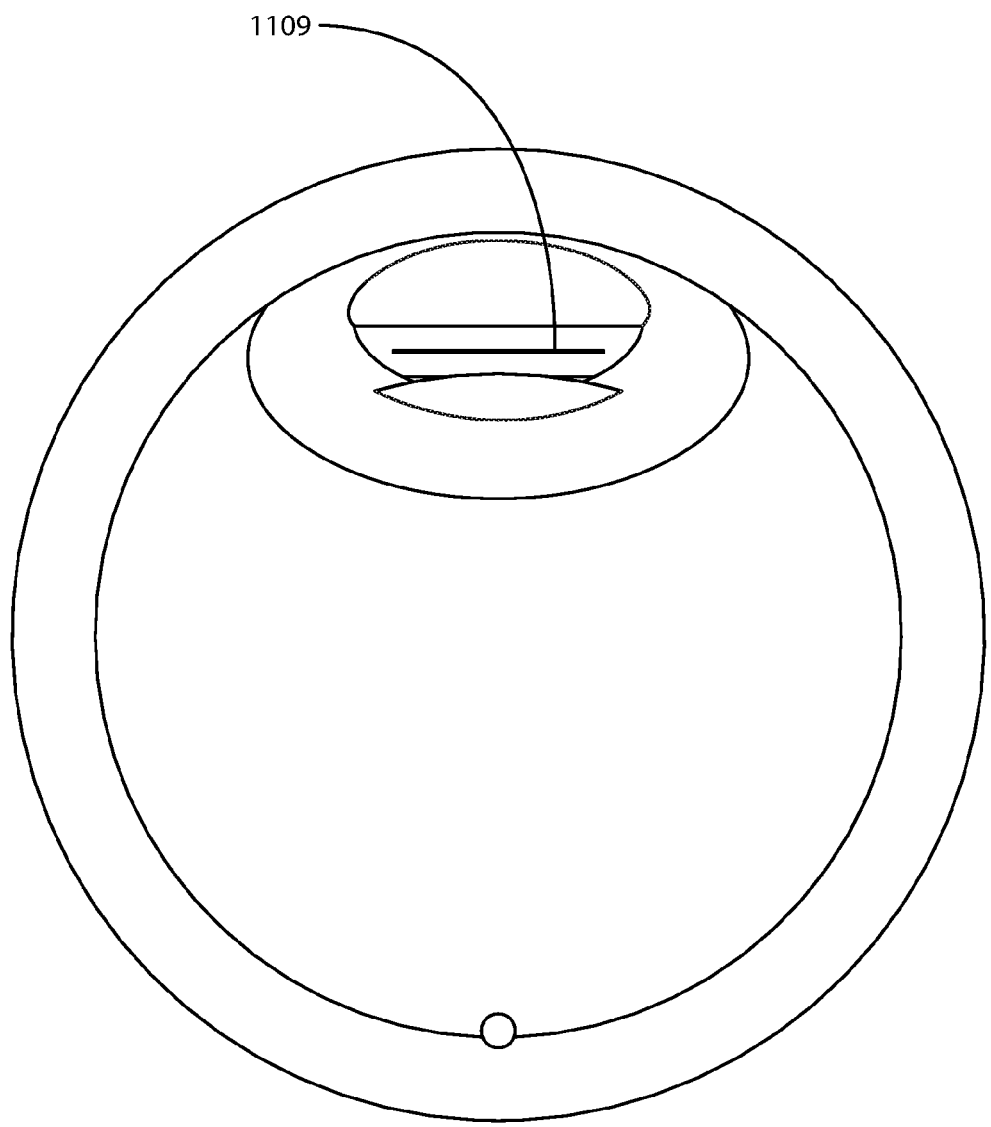
FIG. 15 is a bottom view of an exemplary embodiment of a flexible seal valve and slit.

FIG. 15 is a bottom view of an exemplary embodiment of the flexible seal valve 1105 and slit 1109, according to at least one embodiment of the invention.

Figure 16A:
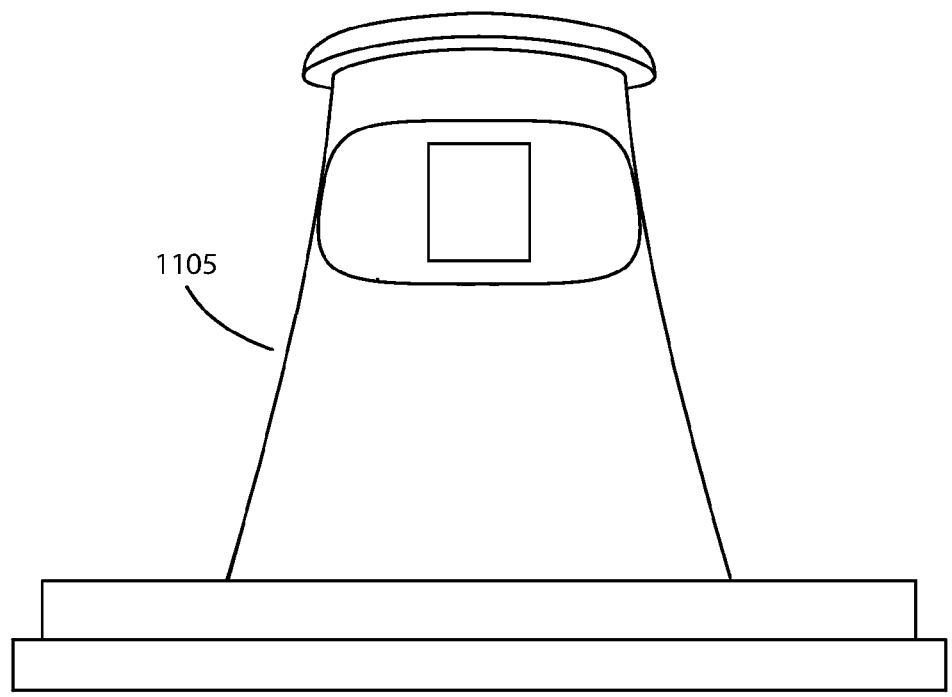
FIG. 16A is a front view of an exemplary embodiment of a flexible seal valve.
Figure 16B:
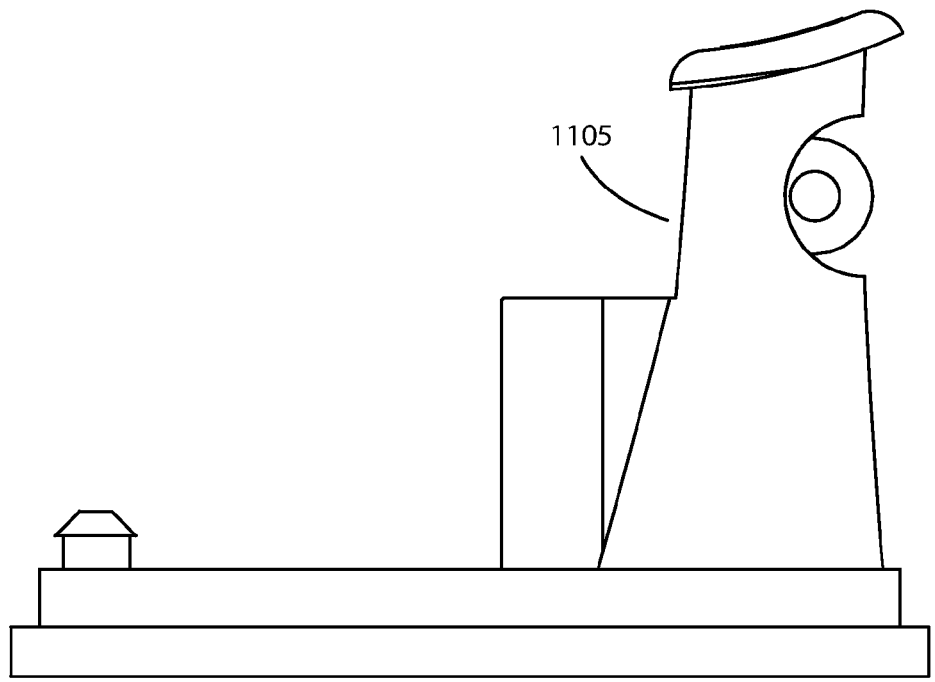
FIG. 16B is a side view of an exemplary embodiment of a flexible seal valve.
Figure 16C:
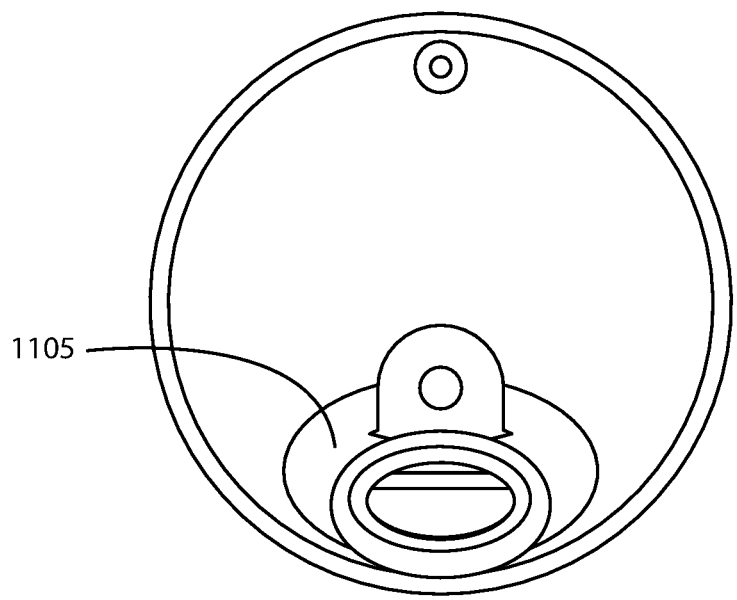
FIG. 16C is a top view of an exemplary embodiment of a flexible seal valve.
Figure 16D:
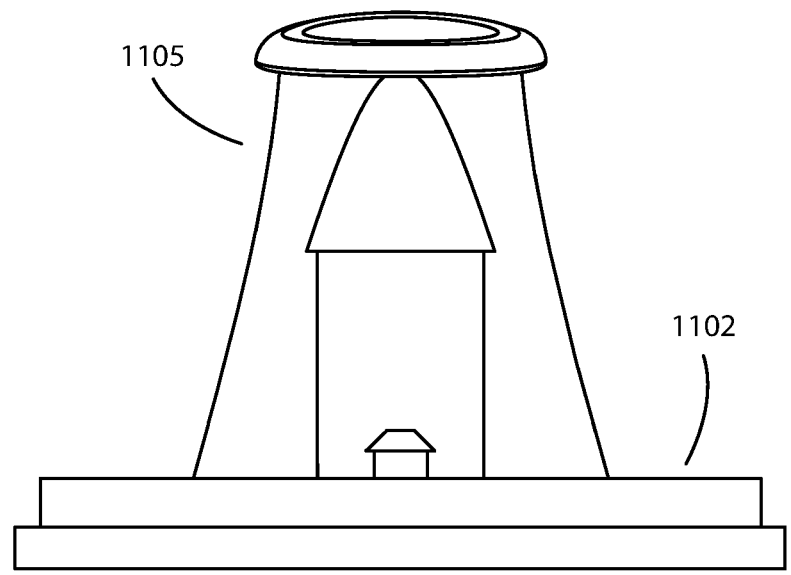
FIG. 16D is a back view of an exemplary embodiment of a flexible seal valve.

FIG. 16A is a front view of a flexible seal valve 1105, FIG. 16B is a side view of the flexible seal valve 1105, FIG. 16C is a top view of the flexible seal valve 1105, and FIG. 16D is a back view of the flexible seal valve 1105, according to one or more embodiments of the invention.

Figure 17A:
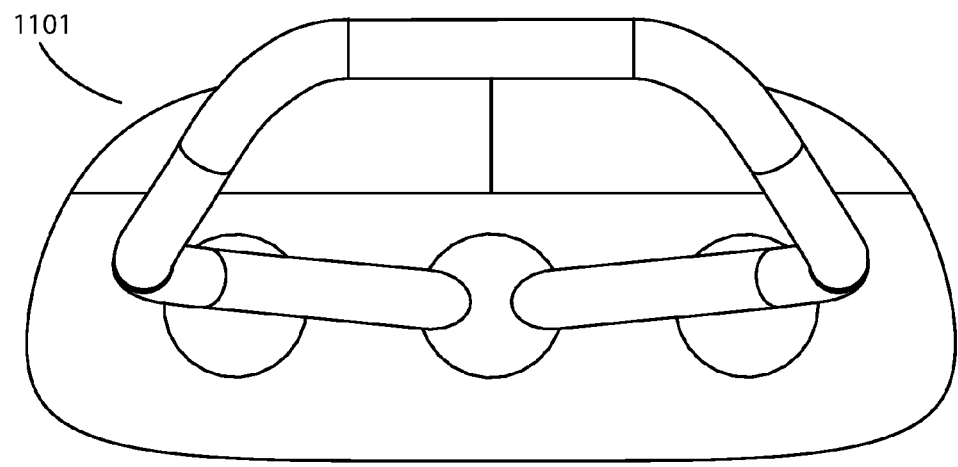
FIG. 17A is a front view of an exemplary embodiment of a button with at least one arm.
Figure 17B:
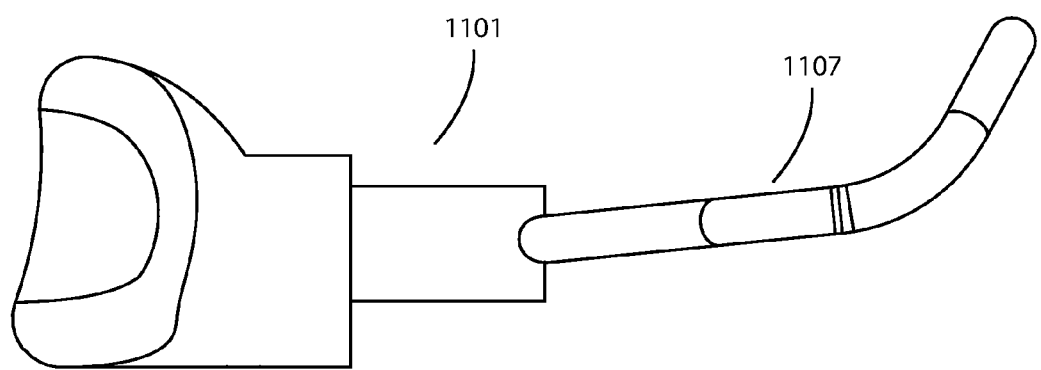
FIG. 17B is a side view of an exemplary embodiment of a button with at least one arm.
Figure 17C:
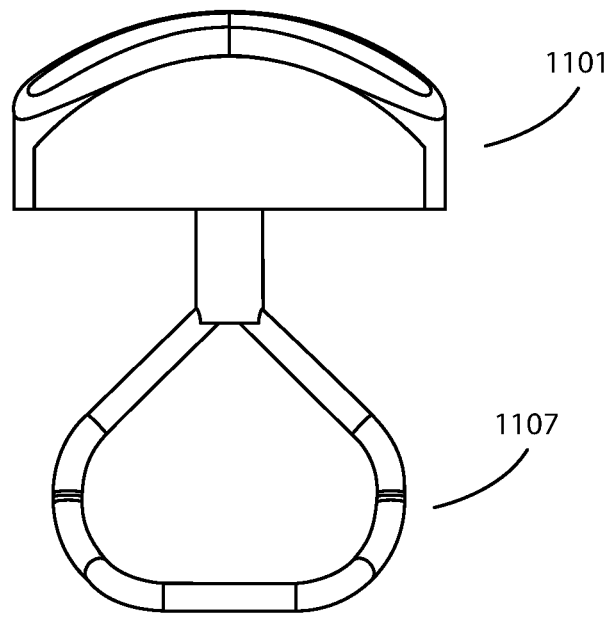
FIG. 17C is a top view of an exemplary embodiment of a button with at least one arm.
Figure 17D:
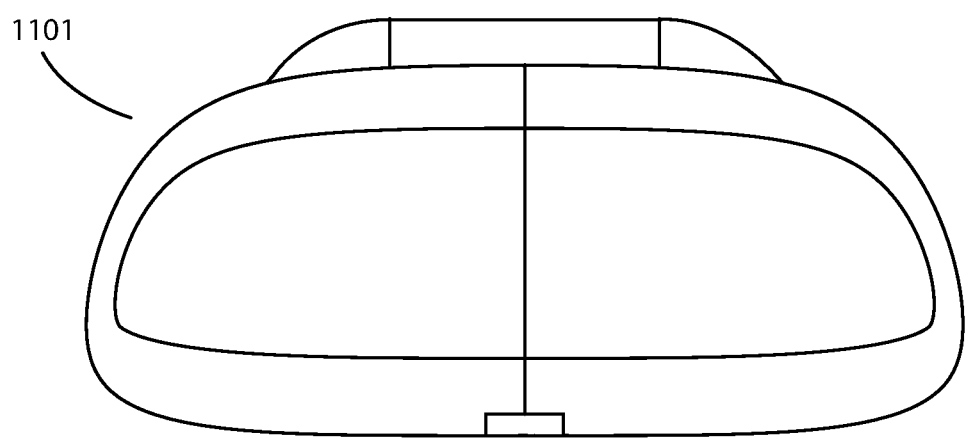
FIG. 17D is a back view of an exemplary embodiment of a button with at least one arm.

FIG. 17A is a front view of a button 1101 with at least one arm 1107, FIG. 17B is a side view of a button 1101 with at least one arm 1107, FIG. 17C is a top view of a button 1101 with at least one arm 1107, and FIG. 17D is a back view of a button with at least one arm, according to one or more embodiments of the invention.

As shown in FIGS. 17A-17D, in one or more embodiments, the at least one arm 1107 of the button 1101 may include a wishbone shaped arm, such that the at least one arm 1107 extends from a first horizontal orientation to a second perpendicular orientation. In at least one embodiment, the at least one arm 1107 may be attached on an opposing side of the flexible seal valve 1105 in order to pull open and closed the slit 1109 to open and close the flexible seal valve 1105.

By way of one or more embodiments, the button 1101 may include two parts such as the first structure including the pressable cap and a second structure including the at least one arm 1107. In at least one embodiment, the first structure may be structured orthogonally to at least a portion of the at least one arm 1107, such that at least a portion of the button 1101 includes a substantially T-shaped structure. In one or more embodiments, the first structure and the second structure of the button 1101 may include a dishwasher-safe plastic material. In at least one embodiment of the invention, the flexible seal valve 1105 may include a dishwasher-safe flexible material such as rubber, silicone, or any other type of elastomer.

Figure 18:
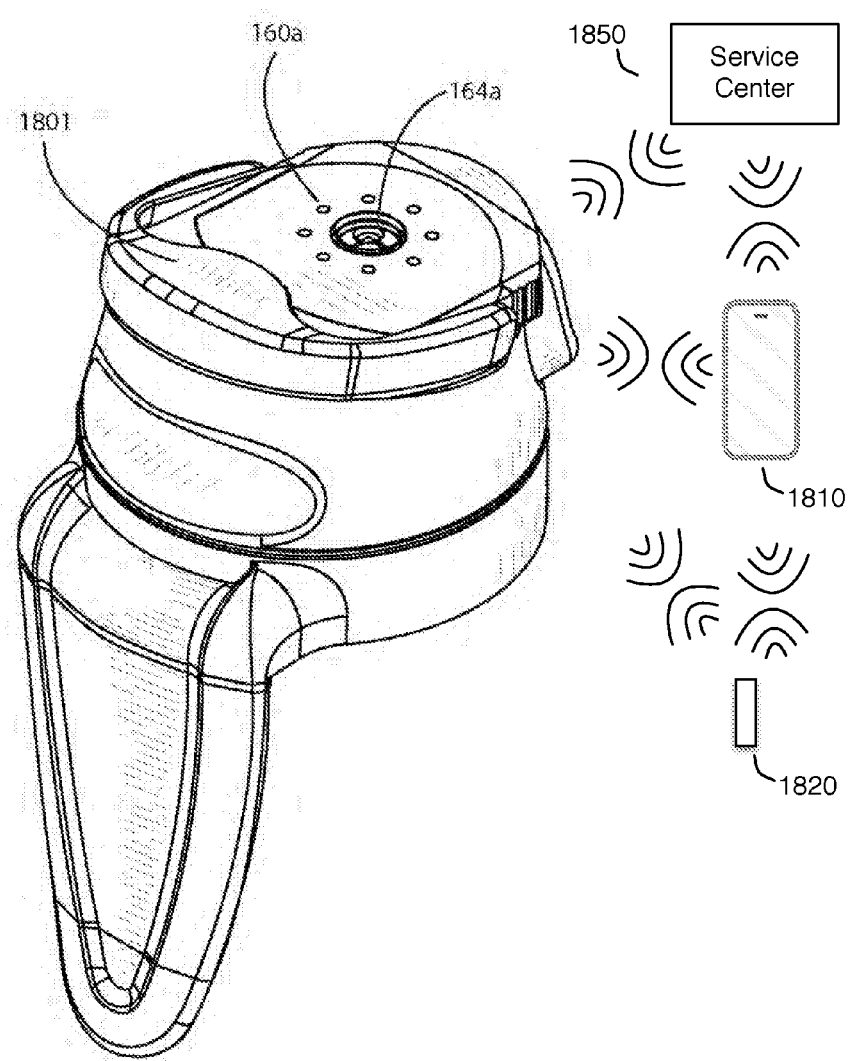
FIG. 18 is a perspective view of an exemplary embodiment of the invention with a handle in a closed position.

FIG. 18 is perspective view of an exemplary embodiment of the system with a handle in a closed position, according to at least one embodiment of the invention. As shown in FIG. 18, one or more embodiments of the invention may include the cap that handle 1801 couples with as shown (See FIG. 7 for another embodiment of the cap) wherein the cap couples with a beverage container. In at least one embodiment, the system may also include the processor coupled with the cap, for example housed within, at least one inclinometer coupled with the processor, and a timer coupled with the processor. In at least one embodiment, the cap may include the at least one display device, shown here as a series of LEDs 160a around a button 164a on top of the cap, wherein the processor may indicate on the at least one display device the volume of fluid dispensed from the beverage container. As shown, embodiments of the invention may wirelessly communicate with an external computer such as a mobile device, or cell phone 1810, or user measurement device 1820, such as a FITBIT® or other tracking sensor. Embodiments may also interface with a Service Center 1850, for example a medical facility, insurance company, employer, or other entity tasked to ensure proper hydration of an individual, for example pre or post surgery. Embodiments may communication hydration information to and from the Service Center to indicate whether or not an individual is properly hydrated, for example before or after surgery. The Service Center may be considered to be any remote entity, including the Cloud, a remote database, a call center, or any other type of entity including emergency services. In one or more embodiments, the Service Center may charge a fee to monitor the hydration levels and/or provide reminders to the individual or other guardians or caretakers that the individual needs fluid for example.

The wireless signals maybe sent between the two computers and the apparatus bi-directionally as shown by the electromagnetic waves between the various components of the system. In at least one embodiment, the cap may include at least one display device, wherein the processor may indicate on the at least one display device 160a the volume of fluid dispensed from the beverage container, and/or indicate when to drink and/or how much to drink. In one or more embodiments, the system may include at least one activity level input that obtains at least one activity level of a user of the beverage container to determine an amount of fluid a user of the beverage container should consume and may indicate the amount of fluid on the at least one display device, for example by flashing an LED until enough liquid has been consumed. Any number of LED's may be flashed in any order in any intensity level for any duration in order to alert the individual. An alert may be sent to the user after a predetermined interval to consume fluid after a previous amount of fluid is dispensed or if the amount of fluid dispensed from the beverage container is below the amount of fluid the user of said beverage container is to consume. Alerts may be displayed locally or remotely or both. Alternatively, or in combination the apparatus may interface to any external user tracking device such as a mobile device or cell phone with an accelerometer, or a FITBIT® user movement measurement device to obtain activity level, calories burned, activity duration and intensity, temperature, heart rate or any other value that the mobile device, cell phone or FITBIT® user measurement device can sense. After obtaining the activity level, calories burned, activity duration and intensity, temperature, heart rate, or any other parameter from any other sensor coupled with the external computer 1810, 1820, the apparatus may alter the amount of fluid that is recommended for user intake based on these values, or for example may obtain a temperature of the environment from the Internet and utilize that value in calculating more or less required liquid intake. For example, if the temperature is over 100 as determined by computer 1810, either with a local sensor or over the Internet, or via user measurement device 1820, then the volume may be increased by 2 ounces per hour for example. If the temperature is less than 60 degrees, then the volume by decreased by 2 ounces per hour. These examples show a rough threshold level of increasing or decreasing logic that the apparatus may employ, however any tables or functions that take any or all parameters such as the user's weight, age, fitness level and environmental values into account are in keeping with the spirit of the invention.

By way of at least one embodiment, the system may include a button, for example 1101 as shown in FIG. 11, wherein the cap may include a base element and top element coupled with the flexible seal valve 1105. In one or more embodiments, the top element may include a hole, shown for example to the left of compartment 1106 on the top of the cap, that the flexible seal valve 1105 is situated within. In at least one embodiment, the system may include a handle 1801 rotatably coupled with the cap.

In various exemplary embodiments of the invention, the cap may be fitted with a display device, such as display device 160 and 160a, for example an LCD screen, to display information to the user. In one or more embodiments, various controls may be positioned at appropriate locations on the cap to select the information to be displayed on display device 160a. In various exemplary embodiments, a control button 164a may be provided, or the display screen 160a may be a touchscreen with controls that are activated by the user's touch or gesture. In at least one embodiment, the display device 160a may include a plurality of indicator lights. In one or more embodiments, the control button 164a may be used to reset the display or program it to output different information. The indicator lights, in one or more embodiments, may be used to indicate the amount of fluid that has been dispensed since the last reset, or over a particular period of time such as a day or a week, by sequentially lighting up as additional fluid is dispensed.

Figure 19:
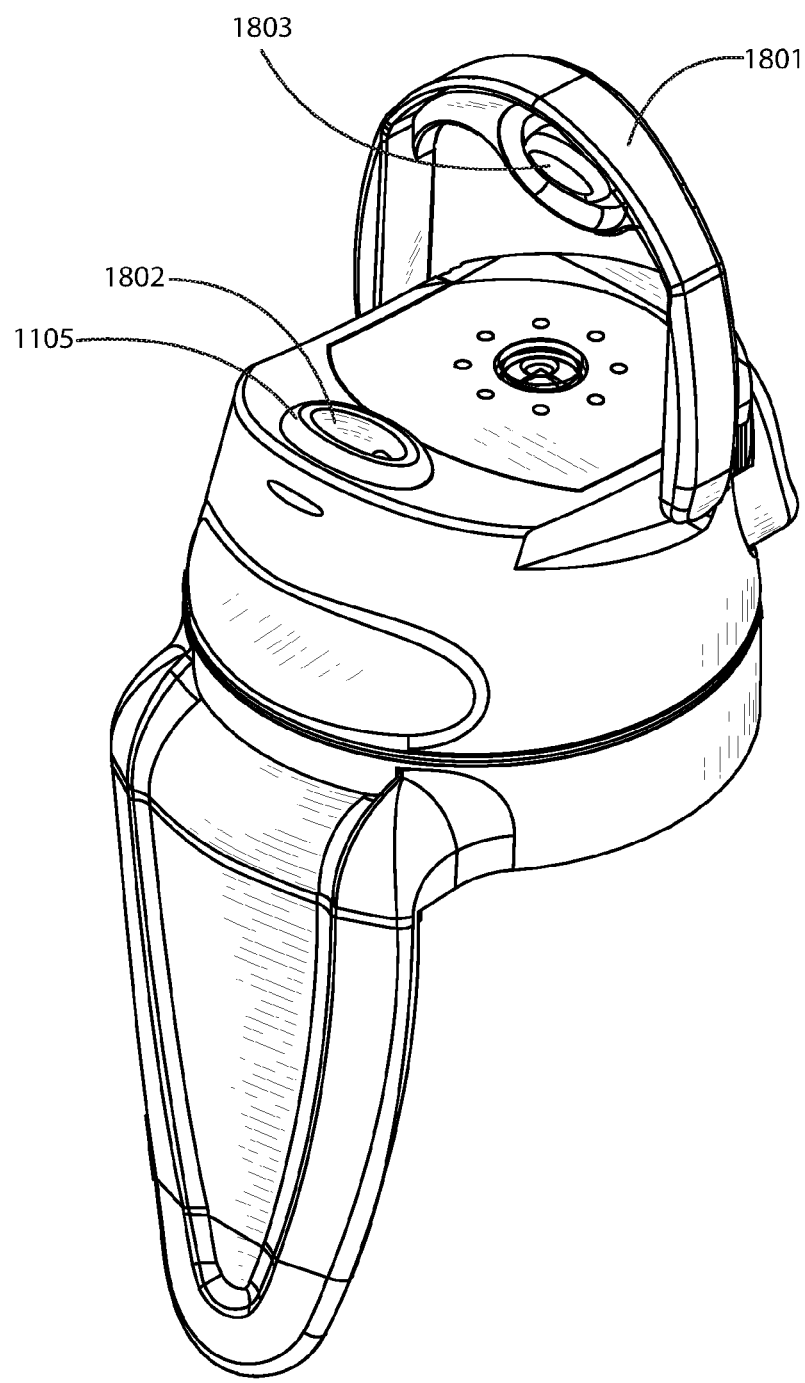
FIG. 19 is a perspective view of an exemplary embodiment of the invention with a handle in a carrying position.
Figure 20:
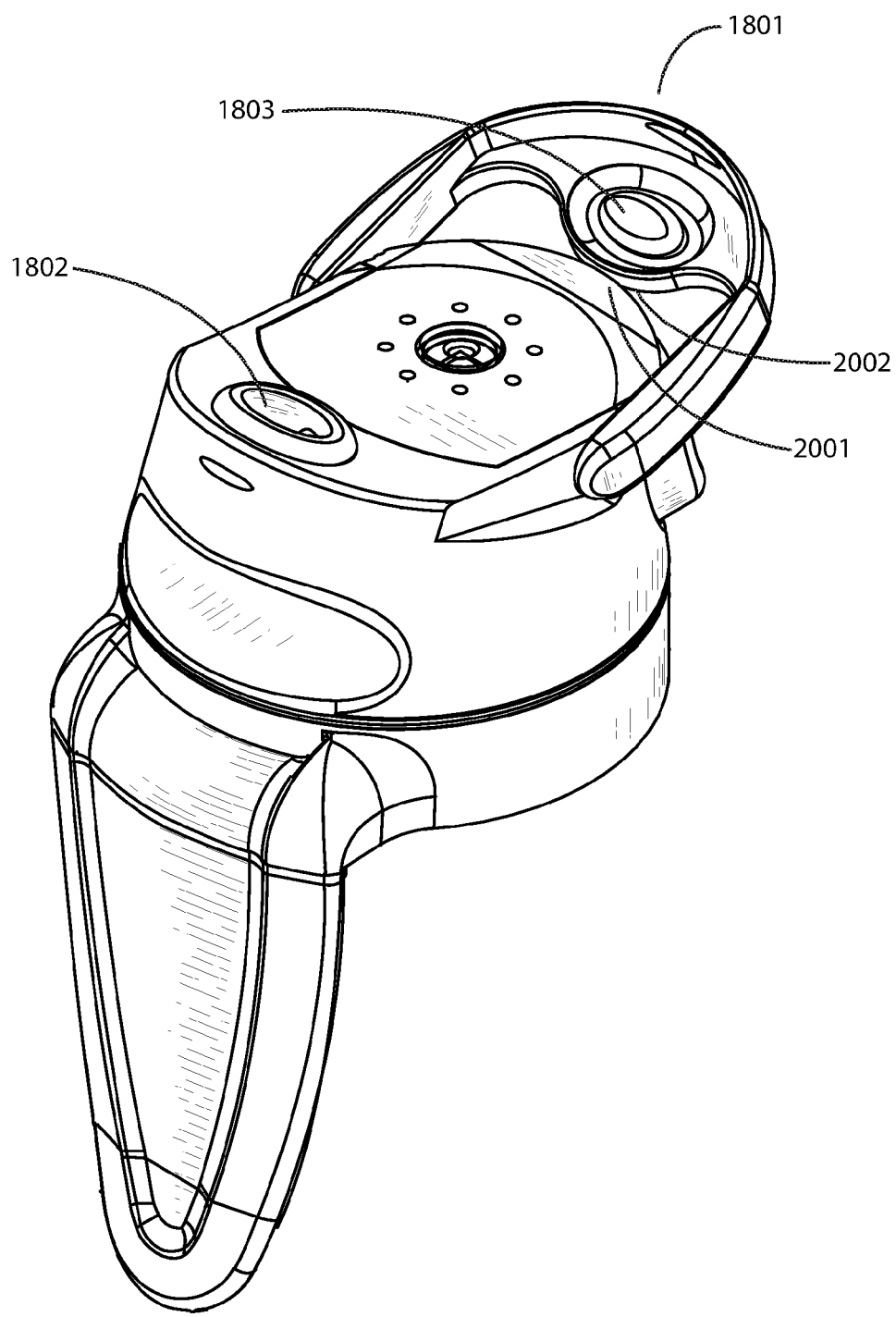
FIG. 20 is a perspective view of an exemplary embodiment of the invention with the handle in an open position.

FIG. 19 is a perspective view of an exemplary embodiment of the system, and FIG. 20 is a perspective view of an exemplary embodiment of the system with the handle in an open position.

By way of at least one embodiment, the system may include the button including the at least one arm, and the flexible seal valve 1105 including the slit 1109, situated beneath the top portion 1802 of the flexible seal valve 1105. In one or more embodiments, the cap is moveably coupled with the button. In at least one embodiment, the flexible seal valve is coupled with the cap. In one or more embodiments, the at least one arm is coupled with the flexible seal valve to operatively open and close the slit in the flexible seal valve when the button is moved in a first and second direction respectively.

In one or more embodiments, the handle 1801 may move from a first closed position on a front end of the cap (as shown in FIG. 18) to a second carrying position (as shown in FIG. 19), and may move to a third open position and in some embodiments optionally snap open or otherwise be held open by a frictional coupling between handle portion 2002 and cap back end 2001 of the cap (as shown in FIG. 20). In at least one embodiment, the back end 2001 is on an opposite end of the cap relative to the front end, wherein the front end may include the flexible seal valve 1105.

In one or more embodiments of the invention, as shown in FIG. 18, in the first closed position the handle 1801 may move to operatively cover the top portion 1802 of the flexible seal valve 1105. By way of at least one embodiment, as shown in FIG. 19, the handle 1801 may include a plug 1803 that one or more of covers top portion 1802 of the flexible seal valve to provide a sanitary covering when the apparatus is carried in a gym bag for example, wherein the plug is covers top 1802, when the handle 1801 is rotated to cover the top portion 1802. In one or more embodiments, the plug 1803 is on a bottom portion of the handle 1801, wherein the plug 1803 is not visible when the handle 1801 is in the first closed position covering the top portion 1802.

In at least one embodiment, in the second carrying position as shown in FIG. 19 and in the third open position as shown in FIG. 20, the handle 1801 may uncover the slit 1105 beneath top portion 1802. As shown in FIG. 20, according to one or more embodiments of the invention, the handle 1801 may include a centered downwardly oriented handle back end 2002 at a top portion of the handle. In at least one embodiment, the handle back end 2002 may be located behind the cap back end 2001 when the handle 1801 is in the third open position, or as previously described, frictionally coupled therewith.

In one or more embodiments, in the third open position, the handle 1801 may couple with and lock at or under the cap back end 2001 via the handle back end 2002. In at least one embodiment, the handle back end 2002 may couple and lock with the cap back end 2001 using one or more coupling flexible elements and holes located on one or more of the cap back end 2001 and the handle back end 2002. As such, in at least one embodiment, the handle 1801 may be positioned in a locked third open position to not interfere with the user during user, such as when the user is consuming the beverage within the container.

In at least one embodiment of the invention, the handle 1801 may include a handle front end located at an opposite side of the handle back end 2002, at the top portion of the handle 1801. In one or more embodiments, the handle front end may couple and lock with the cap front end, such as during the first closed position, for example using a snap on the left side of the cap to the left of the top portion 1802 of the valve that corresponds to snap portion on the inside of the handle shown just to beneath the far right portion of the handle where lead line from 1801 points. Any other mechanism for frictionally coupling the handle and cap in a closed position is in keeping with the spirit of the invention. In at least one embodiment, the handle front end may couple and lock with the cap front end using one or more coupling flexible elements and holes located on one or more of the cap front end and the handle front end. As such, in at least one embodiment, when the handle 1801 is positioned in the first closed position, it may be in a locked and secure first closed position when the user is not consuming the beverage. In one or more embodiments, when the handle is in the first closed position, the second open position and the third open position, the display device 160a, the plurality of indicator lights and the control button 164a remain visible to the user.

FIG. 21 is a structural view of an exemplary embodiment of a volume sensing beverage container cap system for a beverage. As shown in FIG. 21, one or more embodiments of the invention discussed above may include one or more of the at least one electronic device 1103, the at least one communication device 2111, the start button or button interface 2112, (which may couple with a switch and/or button external to the electronic package for example), the processor 2113, the at least one displace device 2114, the timer 2115 (whether external or as also shown, internal to processor 2113 or tightly coupled thereto) and the at least one sensor 2116. Embodiments may also include a speaker and/or other input/output acoustic device 2118. Although shown outside of element 1103, timer 2115 and sensor 2116 may be integrated within electronic element 1103 or use an external timer or sensor, for example as obtained from a mobile device such as a cell phone. In this manner, the time and accelerometer may be utilized as the activity level sensor in one or more embodiments. Other embodiments may utilize internal or external timer 2115 and sensor 2116 in combination with an external mobile device and correlate movement information as determined internally via the tilt sensor and timer, for example to calibrate the activity level for one or more individuals.

In one or more embodiments, the ability to store data local to the apparatus and use the data locally and transmit and receive data from the external device when connected wirelessly is referred to herein as "dual mode". In one or more embodiments a personal profile for a user may be synchronized when the apparatus is connected to the external device. The personal profile may include goals, alarms, silent or sound enabled modes, night or quiet modes where alarms are silenced while the apparatus continues to track consumption and/or hydration values. At each synchronization time, the personal profile parameters are updated. In this manner, the apparatus may operate autonomously and when connected, make use of the capabilities of the external device, which may include enhanced display and processing capabilities for example.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. A fluid consumption monitoring system comprising:
   a housing configured to couple with a beverage container wherein said housing comprises
      an opening that dispenses contents of said beverage container;
      a moveable seal that closes said opening; and,
      one or more sensors coupled with said housing or that extend into said beverage container;
   a wireless communication interface coupled with said housing;
   a memory coupled with said housing; and,
   a processor coupled with said memory and said wireless communication interface and situated in said housing wherein said processor is configured to
      receive sensor data from said one or more sensors;
      calculate at least one of an amount of fluid inside of, an amount of fluid dispensed from or an amount of fluid added to said beverage container from said sensor data;
      store said amount of fluid in said memory; and,
      transmit said amount of fluid dispensed from said beverage container when a wireless communication channel is available to an external device.

2. The system of claim 1, further comprising a display coupled to said processor and configured to indicate said amount of fluid dispensed from said beverage container.

3. The system of claim 1, wherein said external device is a smartphone, a tablet computer, a laptop, or a cloud-based system.

4. The system of claim 1, wherein said one or more sensors comprise one or more of a capacitance probe, a resistance probe, an ultrasonic sensor, an optical sensor, a mechanical float, a pressure sensor or a weight sensor.

5. The system of claim 1, wherein said processor is further configured to estimate an amount of fluid inside of, an amount of fluid dispensed from or an amount of fluid added to said beverage container.

6. The system of claim 5, wherein said one or more sensors comprise a tilt sensor or inclinometer.

7. The system of claim 6, further comprising a valve and a timer that measures how long said valve is open and wherein said processor is further configured to estimate an amount of fluid dispensed from said beverage container based on data from said tilt sensor or inclinometer and said timer in combination with a predetermined size of said opening in said housing configured to dispense said liquid.

8. The system of claim 5, wherein said tilt sensor or inclinometer is also utilized to calculate an activity level based on changes in tilt over time.

9. The system of claim 1, wherein said processor resets said amount of fluid dispensed from said beverage container at a regular time interval.

10. The system of claim 1, wherein said one or more sensors comprise one or more of an accelerometer, a gyroscope, a GPS system, a pedometer, a thermometer, a physiological monitor, a heart rate sensor, a respiration rate sensor, a blood pressure sensor, a blood oxygen level sensor, a hydration sensor, a humidity sensor, an altitude sensor, and a barometric pressure sensor.

11. The system of claim 2, wherein said display is further configured to display an activity level of a user of said beverage container.

12. The system of claim 1, wherein said moveable seal comprises
   a cover, or
   a valve and wherein said beverage container further comprises a valve button that activates said valve.

13. The system of claim 1, wherein
   said processor or said external device is further configured to
      accept or obtain values for one or more factors affecting fluid requirements; and,
      calculate an amount of fluid a user of said beverage container is to consume based on said values for one or more factors affecting fluid requirements.

14. The system of claim 2, wherein
   said display is further configured to display an amount of fluid said user of said beverage container has consumed, or is to consume, or both, in a predetermined amount of time.

15. The system of claim 14, wherein said processor is further configured to
   alert said user after a predetermined interval to consume fluid after a previous amount of fluid is dispensed, or
   alert said user if said amount of fluid dispensed from said beverage container is below said amount of fluid said user of said beverage container is to consume.

16. The system of claim 13, wherein said one or more factors affecting fluid requirements comprise
   one or more of an age of said user, weight of said user, temperature, humidity, sunny or cloudy value, activity level, time of day or time since last drink, activity level, motion, altitude, medical needs, number of steps, heart rate, respiration rate, blood pressure, blood oxygen level, and a hydration value obtained from the user.

17. The system of claim 13, wherein
   said one or more factors affecting fluid requirements comprise an activity level; and,
   said one or more sensors comprise an activity level input sensor that measures said activity level.

18. The system of claim 13, wherein
   said one or more factors affecting fluid requirements comprise an external temperature; and,
   said one or more sensors comprise a thermometer that measures said external temperature or receives external temperature data from said wireless communication interface.

19. The system of claim 13, further comprising
   a timer; and,
   at least one sound emitting device;
   wherein
      said at least one sound emitting device beeps to indicate one or more time periods to consume fluid as determined by said timer and whether enough fluid has been consumed by the user as determined by said one or more sensors; and, said at least one sound emitting device remains to beep until enough fluid has been consumed by the user at said one or more time periods as determined by said timer and said one or more sensors.

20. The system of claim 1, wherein said processor is further configured to synchronize personal profile parameters when said wireless communication channel is available to said external device.

* * * * *